United States Patent
Berthon-Jones

Patent Number: 6,138,675
Date of Patent: *Oct. 31, 2000

[54] DETERMINATION OF THE OCCURRENCE OF AN APNEA

[75] Inventor: Michael Berthon-Jones, Leonay, Australia

[73] Assignee: Resmed Ltd., Australia

[*] Notice: This patent is subject to a terminal disclaimer.

[21] Appl. No.: 08/931,439

[22] Filed: Sep. 16, 1997

Related U.S. Application Data

[63] Continuation of application No. 08/335,118, Nov. 4, 1994, Pat. No. 5,704,345.

[30] Foreign Application Priority Data

Nov. 5, 1993 [AU] Australia .................. PM2246

[51] Int. Cl.⁷ .................................................. A61M 16/00
[52] U.S. Cl. .............................. 128/204.23; 128/204.21; 128/204.18; 600/529
[58] Field of Search .................... 128/204.23, 204.21, 128/204.18, 205.23, 201.48, 204.24; 600/529, 484, 521

[56] References Cited

U.S. PATENT DOCUMENTS

| | | |
|---|---|---|
| Re. 35,295 | 7/1996 | Estes et al. . |
| 2,904,033 | 9/1959 | Shane . |
| 3,559,638 | 2/1971 | Potter . |
| 3,595,228 | 7/1971 | Simon et al. . |
| 3,611,801 | 10/1971 | Paine et al. . |
| 3,726,270 | 4/1973 | Griffis et al. . |
| 3,802,417 | 4/1974 | Lang . |
| 3,817,246 | 6/1974 | Weigl . |
| 3,882,847 | 5/1975 | Jacobs . |
| 3,903,875 | 9/1975 | Hughes . |
| 3,914,994 | 10/1975 | Banner . |
| 3,932,054 | 1/1976 | McKelvey . |
| 3,961,627 | 6/1976 | Ernst et al. . |
| 3,985,467 | 10/1976 | Lefferson . |
| 3,989,037 | 11/1976 | Franetzki . |

(List continued on next page.)

FOREIGN PATENT DOCUMENTS

| | | |
|---|---|---|
| 59270/90 | 12/1990 | Australia . |
| 62221/90 | 3/1991 | Australia . |
| 76019/91 | 1/1992 | Australia . |
| 33877/93 | 4/1993 | Australia . |
| 48748/93 | 12/1993 | Australia . |
| 52628/93 | 7/1994 | Australia . |
| 34471/95 | 2/1996 | Australia . |
| 40711-95 | 4/1996 | Australia . |
| 39130/95 | 6/1996 | Australia . |

OTHER PUBLICATIONS

Derwent: Flowmeter for fliuids–has turbine transducer and volumetric sensor for simuultaneous calibration.

*Primary Examiner*—John G. Weiss
*Assistant Examiner*—V. Srivastava
*Attorney, Agent, or Firm*—Gottlieb, Rackman and Reisman

[57] ABSTRACT

Methods and apparatus for determining the occurrence of an apnea, patency and/or partial obstruction of the airway are disclosed. Respiratory air flow from a patient is measured to give an air flow signal. The determination of an apnea is performed by calculating the variance of the air flow signal over a moving time window and comparing the variance with a threshold value. One determination of partial obstruction of the airway is performed by detecting the inspiratory part of the air flow signal, scaling it to unity duration and area and calculating an index value of the amplitude of the scaled signal over a mid-portion. Alternatively, the index value is a measure of the flatness of the air flow signal over the mid-portion. One determination of patency of the airway is performed by applying an oscillatory pressure waveform of known frequency to a patient's airway, calculating the magnitude of the component of said air flow signal at the known frequency induced by the oscillatory pressure waveform and comparing the calculated magnitude with a threshold value. Alternatively, the air flow signal is analysed to detect the presence of a component due to cardiogenic activity.

21 Claims, 20 Drawing Sheets

U.S. PATENT DOCUMENTS

| | | |
|---|---|---|
| 4,006,634 | 2/1977 | Billette et al. . |
| 4,077,404 | 3/1978 | Elam . |
| 4,083,245 | 4/1978 | Osborn . |
| 4,206,754 | 6/1980 | Cox et al. . |
| 4,312,235 | 1/1982 | Daigle . |
| 4,320,766 | 3/1982 | Alihanka et al. . |
| 4,322,594 | 3/1982 | Brisson . |
| 4,365,636 | 12/1982 | Barker . |
| 4,381,788 | 5/1983 | Douglas . |
| 4,387,722 | 6/1983 | Kearns . |
| 4,414,982 | 11/1983 | Durkan . |
| 4,433,693 | 2/1984 | Hochstein . |
| 4,440,177 | 4/1984 | Anderson et al. . |
| 4,448,058 | 5/1984 | Jaffe et al. . |
| 4,481,944 | 11/1984 | Bunnell . |
| 4,499,914 | 2/1985 | Schebler . |
| 4,506,666 | 3/1985 | Durkan . |
| 4,519,399 | 5/1985 | Hori . |
| 4,550,615 | 11/1985 | Grant . |
| 4,550,726 | 11/1985 | McEwen . |
| 4,558,710 | 12/1985 | Eichler . |
| 4,570,631 | 2/1986 | Durkan . |
| 4,576,179 | 3/1986 | Manus et al. . |
| 4,580,575 | 4/1986 | Birnbaum et al. . |
| 4,595,016 | 6/1986 | Fertig et al. . |
| 4,602,644 | 7/1986 | DiBenedetto et al. . |
| 4,630,614 | 12/1986 | Atlas . |
| 4,648,396 | 3/1987 | Raemer . |
| 4,648,407 | 3/1987 | Sackner . |
| 4,655,213 | 4/1987 | Rapoport et al. . |
| 4,677,975 | 7/1987 | Edgar et al. . |
| 4,686,974 | 8/1987 | Sato et al. . |
| 4,686,999 | 8/1987 | Snyder et al. . |
| 4,723,543 | 2/1988 | Beran . |
| 4,738,266 | 4/1988 | Thatcher . |
| 4,747,403 | 5/1988 | Gluck et al. . |
| 4,777,962 | 10/1988 | Watson et al. . |
| 4,777,963 | 10/1988 | McKenna . |
| 4,795,314 | 1/1989 | Prybella et al. . |
| 4,802,485 | 2/1989 | Bowers et al. . |
| 4,803,471 | 2/1989 | Rowland . |
| 4,819,629 | 4/1989 | Jonson . |
| 4,823,788 | 4/1989 | Smith et al. . |
| 4,825,802 | 5/1989 | Le Bec . |
| 4,827,922 | 5/1989 | Champain et al. . |
| 4,838,258 | 6/1989 | Dryden et al. . |
| 4,844,085 | 7/1989 | Gattinoni . |
| 4,860,766 | 8/1989 | Sackner . |
| 4,870,960 | 10/1989 | Hradek . |
| 4,887,607 | 12/1989 | Beatty . |
| 4,915,103 | 4/1990 | Visveshwara et al. . |
| 4,928,684 | 5/1990 | Breitenfelder et al. . |
| 4,938,210 | 7/1990 | Shene . |
| 4,938,212 | 7/1990 | Gnook et al. . |
| 4,957,107 | 9/1990 | Sipin . |
| 4,960,118 | 10/1990 | Pennock . |
| 4,971,065 | 11/1990 | Pearce . |
| 4,972,842 | 11/1990 | Korten et al. . |
| 4,982,738 | 1/1991 | Griebel . |
| 4,986,269 | 1/1991 | Hakkinen . |
| 4,989,599 | 2/1991 | Carter . |
| 5,024,219 | 6/1991 | Dietz . |
| 5,046,491 | 9/1991 | Derrick . |
| 5,048,515 | 9/1991 | Sanso . |
| 5,052,400 | 10/1991 | Dietz . |
| 5,063,922 | 11/1991 | Hakkinen . |
| 5,063,938 | 11/1991 | Beck et al. . |
| 5,065,756 | 11/1991 | Rapoport . |
| 5,069,222 | 12/1991 | McDonald, Jr. . |
| 5,090,248 | 2/1992 | Cimmino et al. . |
| 5,099,837 | 3/1992 | Russel, Sr. et al. . |
| 5,105,354 | 4/1992 | Nishimura . |
| 5,107,830 | 4/1992 | Younes . |
| 5,107,831 | 4/1992 | Halpern et al. . |
| 5,129,390 | 7/1992 | Chopin et al. . |
| 5,134,995 | 8/1992 | Gruenke et al. . |
| 5,146,918 | 9/1992 | Kallok et al. . |
| 5,148,802 | 9/1992 | Sanders et al. ............... 128/204.18 |
| 5,161,541 | 11/1992 | Bowman et al. . |
| 5,170,798 | 12/1992 | Riker . |
| 5,174,287 | 12/1992 | Kallok et al. . |
| 5,178,138 | 1/1993 | Walstrom et al. . |
| 5,178,151 | 1/1993 | Sackner . |
| 5,190,048 | 3/1993 | Wilkinson . |
| 5,195,528 | 3/1993 | Hok . |
| 5,199,424 | 4/1993 | Sullivan et al. . |
| 5,203,343 | 4/1993 | Axe et al. . |
| 5,231,983 | 8/1993 | Matson et al. . |
| 5,233,983 | 8/1993 | Markowitz . |
| 5,239,994 | 8/1993 | Atkins . |
| 5,239,995 | 8/1993 | Estes et al. .................. 128/204.23 |
| 5,245,995 | 9/1993 | Sullivan et al. . |
| 5,259,373 | 11/1993 | Gruenke et al. . |
| 5,280,784 | 1/1994 | Kohler . |
| 5,293,864 | 3/1994 | McFadden . |
| 5,295,491 | 3/1994 | Gevins . |
| 5,303,698 | 4/1994 | Tobia et al. . |
| 5,303,700 | 4/1994 | Weismann et al. . |
| 5,311,875 | 5/1994 | Stasz . |
| 5,313,937 | 5/1994 | Zdrojkowski . |
| 5,322,057 | 6/1994 | Raabe et al. . |
| 5,327,899 | 7/1994 | Harris et al. . |
| 5,335,654 | 8/1994 | Rapoport . |
| 5,353,788 | 10/1994 | Miles . |
| 5,360,008 | 11/1994 | Campbell, Jr. . |
| 5,373,842 | 12/1994 | Olsson et al. . |
| 5,388,571 | 2/1995 | Roberts et al. . |
| 5,394,882 | 3/1995 | Mawhinney . |
| 5,400,777 | 3/1995 | Olsson et al. . |
| 5,404,871 | 4/1995 | Goodman et al. . |
| 5,413,111 | 5/1995 | Wilkinson . |
| 5,433,193 | 7/1995 | Sanders et al. . |
| 5,438,980 | 8/1995 | Phillips . |
| 5,443,061 | 8/1995 | Champain et al. . |
| 5,443,075 | 8/1995 | Holscher . |
| 5,448,996 | 9/1995 | Bellin et al. . |
| 5,458,137 | 10/1995 | Axe et al. . |
| 5,479,920 | 1/1996 | Piper et al. . |
| 5,479,939 | 1/1996 | Ogino . |
| 5,483,969 | 1/1996 | Testerman et al. . |
| 5,490,502 | 2/1996 | Rapoport et al. . |
| 5,503,146 | 4/1996 | Froehlich et al. . |
| 5,507,282 | 4/1996 | Younes . |
| 5,509,404 | 4/1996 | Lloyd et al. . |
| 5,509,414 | 4/1996 | Hok . |
| 5,513,631 | 5/1996 | McWilliams . |
| 5,522,382 | 6/1996 | Sullivan et al. ............... 128/204.23 |
| 5,535,738 | 7/1996 | Estes et al. . |
| 5,535,739 | 7/1996 | Rapoport et al. . |
| 5,540,219 | 7/1996 | Mechlenburg et al. . |
| 5,540,220 | 7/1996 | Gropper . |
| 5,540,733 | 7/1996 | Testerman et al. . |
| 5,546,933 | 8/1996 | Rapoport et al. . |
| 5,546,952 | 8/1996 | Erickson . |
| 5,549,106 | 8/1996 | Gruenke et al. . |
| 5,549,655 | 8/1996 | Erickson . |
| 5,551,419 | 9/1996 | Froehlich et al. . |
| 5,558,099 | 9/1996 | Bowman et al. . |
| 5,570,682 | 11/1996 | Johnson . |
| 5,588,439 | 12/1996 | Hollub . |
| 5,598,838 | 2/1997 | Servidio et al. . |
| 5,605,151 | 2/1997 | Lynn . |

| | | |
|---|---|---|
| 5,608,647 | 3/1997 | Rubsamen et al. . |
| 5,630,411 | 5/1997 | Holscher . |
| 5,642,730 | 7/1997 | Baran . |
| 5,647,351 | 7/1997 | Wesimann et al. . |
| 5,655,520 | 8/1997 | Howe et al. . |
| 5,660,171 | 8/1997 | Kimm et al. . |
| 5,666,946 | 9/1997 | Langenback . |
| 5,701,883 | 12/1997 | Hete et al. . |
| 5,704,345 | 1/1998 | Berthon-Jones ........... 128/204.23 |
| 5,730,121 | 3/1998 | Hawkins, Jr. et al. . |
| 5,797,852 | 8/1998 | Karakasoglu et al. . |
| 5,803,066 | 9/1998 | Rapoport et al. . |
| 5,845,636 | 12/1998 | Gruenke et al. . |

FOREIGN PATENT DOCUMENTS

| | | |
|---|---|---|
| 0 066 451 A1 | 12/1982 | European Pat. Off. . |
| 0 164 500 A2 | 3/1985 | European Pat. Off. . |
| 0 171 321 A1 | 2/1986 | European Pat. Off. . |
| 0 236 850 A2 | 9/1987 | European Pat. Off. . |
| 298 367 A2 | 1/1989 | European Pat. Off. . |
| 0 425 092 A1 | 9/1989 | European Pat. Off. . |
| 0 452 001 A2 | 3/1990 | European Pat. Off. . |
| 0 461 281 A1 | 12/1991 | European Pat. Off. . |
| 481 459 A1 | 4/1992 | European Pat. Off. . |
| 0514 744 | 11/1992 | European Pat. Off. . |
| 606 687 A2 | 7/1994 | European Pat. Off. . |
| 0651971 A1 | 5/1995 | European Pat. Off. . |
| 0 656 216 A2 | 6/1995 | European Pat. Off. . |
| 178 925 A2 | 4/1996 | European Pat. Off. . |
| 0 714 670 A2 | 6/1996 | European Pat. Off. . |
| 0 765 631 A2 | 4/1997 | European Pat. Off. . |
| 0 788 805 A2 | 8/1997 | European Pat. Off. . |
| 0 839 545 A1 | 5/1998 | European Pat. Off. . |
| 2 672 221 | 8/1992 | France . |
| 2682042 A1 | 4/1993 | France . |
| 3015279 A1 | 10/1981 | Germany . |
| 3345067 A1 | 6/1984 | Germany . |
| 3429345 A1 | 6/1985 | Germany . |
| 3537507 A1 | 4/1987 | Germany . |
| 296 12 119 U1 | 12/1996 | Germany . |
| 195 36 632 A1 | 3/1997 | Germany . |
| 54-104369 | 8/1979 | Japan . |
| 62-103297 | 4/1987 | Japan . |
| 63-275352 | 11/1988 | Japan . |
| 4-70516 | 3/1992 | Japan . |
| 8019610 | 1/1996 | Japan . |
| 467041 | 5/1992 | Sweden . |
| 1432572 | 4/1976 | United Kingdom . |
| 1583273 | 1/1981 | United Kingdom . |
| 2 077 444 | 12/1981 | United Kingdom . |
| 2 164 569 | 3/1986 | United Kingdom . |
| 2 166 871 | 5/1986 | United Kingdom . |
| 2 221 302 | 1/1990 | United Kingdom . |
| 2 254 700 | 10/1992 | United Kingdom . |
| 2 261 290 | 5/1993 | United Kingdom . |
| 2 294 400 | 5/1996 | United Kingdom . |
| WO 82/03326 | 10/1982 | WIPO . |
| WO 82/03548 | 10/1982 | WIPO . |
| WO 86/05965 | 10/1986 | WIPO . |
| WO 86/06969 | 12/1986 | WIPO . |
| WO 87/02577 | 5/1987 | WIPO . |
| WO 89/09565 | 10/1988 | WIPO . |
| WO 88/10108 | 12/1988 | WIPO . |
| WO 90/14121 | 1/1990 | WIPO . |
| WO 90/09146 | 8/1990 | WIPO . |
| WO 91/12051 | 8/1991 | WIPO . |
| WO 91/19456 | 12/1991 | WIPO . |
| WO 92/11054 | 7/1992 | WIPO . |
| WO 92/15353 | 9/1992 | WIPO . |
| WO 92/22244 | 12/1992 | WIPO . |
| WO 93/08857 | 5/1993 | WIPO . |
| WO 93/09834 | 5/1993 | WIPO . |
| WO 93/21982 | 11/1993 | WIPO . |
| WO 93/24169 | 12/1993 | WIPO . |
| WO 94/04071 | 3/1994 | WIPO . |
| WO 94/16759 | 8/1994 | WIPO . |
| WO 94/20018 | 9/1994 | WIPO . |
| WO 94/22517 | 10/1994 | WIPO . |
| WO 94/23780 | 10/1994 | WIPO . |
| WO 95/32016 | 11/1995 | WIPO . |
| WO 95/34917 | 12/1995 | WIPO . |
| WO 96/16688 | 6/1996 | WIPO . |
| WO 96/32055 | 10/1996 | WIPO . |
| WO 96/36279 | 11/1996 | WIPO . |
| WO 96/40337 | 12/1996 | WIPO . |
| WO 96/41571 | 12/1996 | WIPO . |
| WO 97/05824 | 2/1997 | WIPO . |
| WO 97/10019 | 3/1997 | WIPO . |
| WO 97/14354 | 4/1997 | WIPO . |
| WO 97/15343 | 5/1997 | WIPO . |
| WO 97/18752 | 5/1997 | WIPO . |
| WO 97/20499 | 6/1997 | WIPO . |
| WO 97/22377 | 6/1997 | WIPO . |
| WO 98/04311 | 2/1998 | WIPO . |
| WO 98/52467 | 11/1998 | WIPO . |

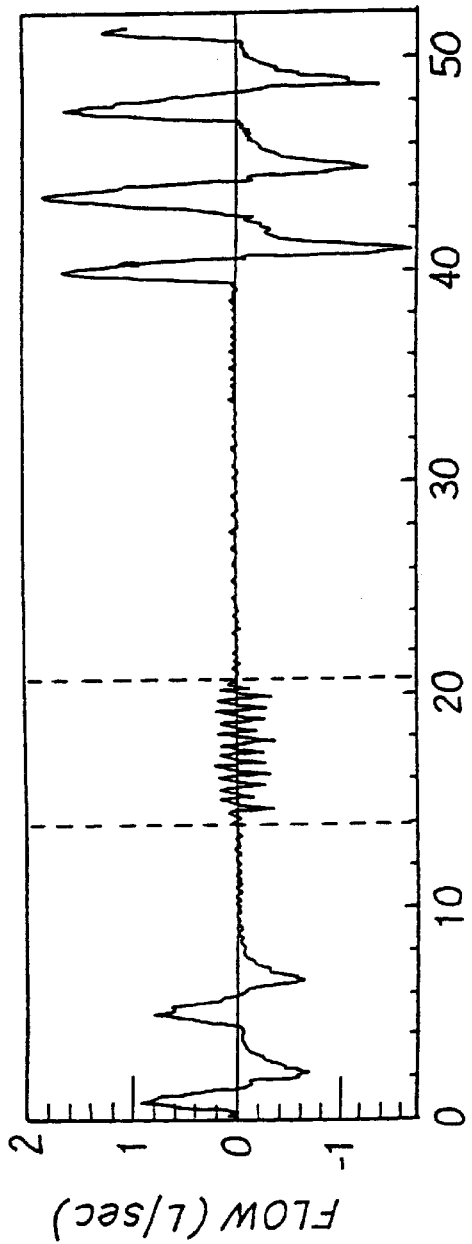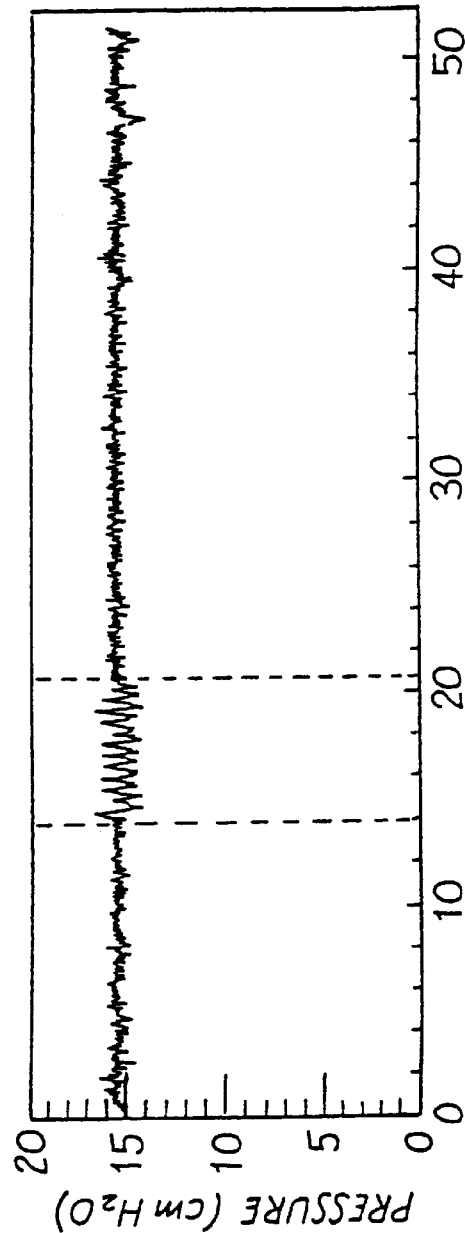

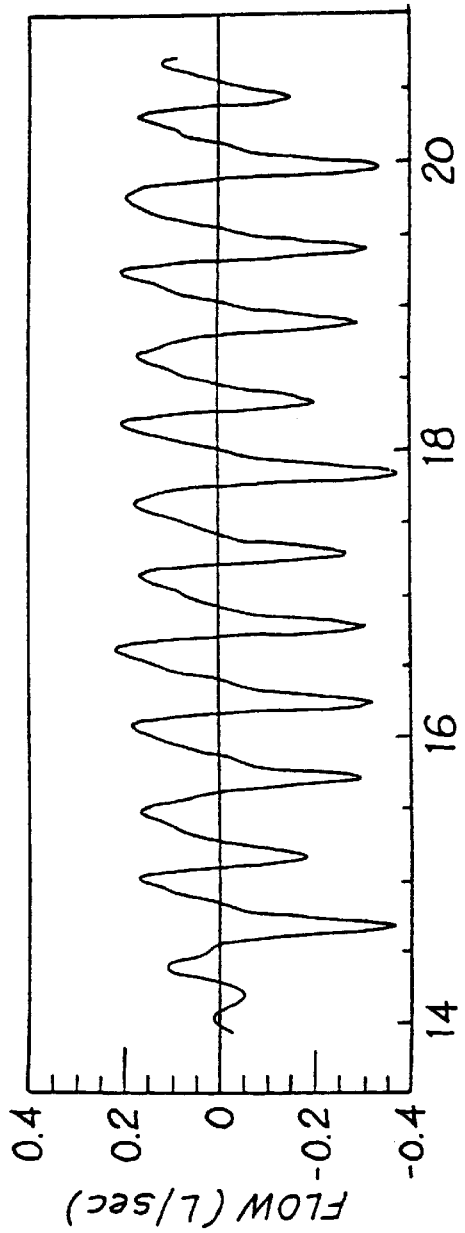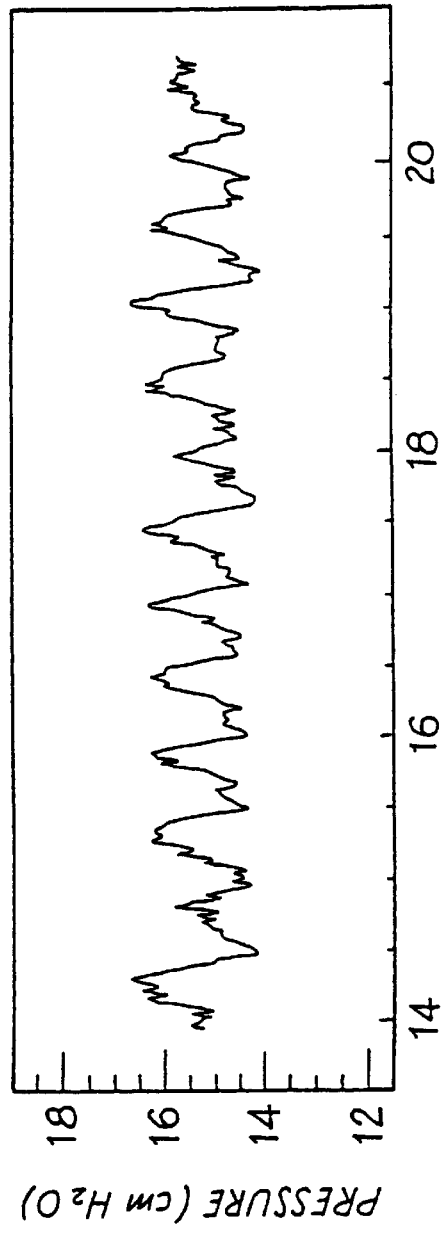

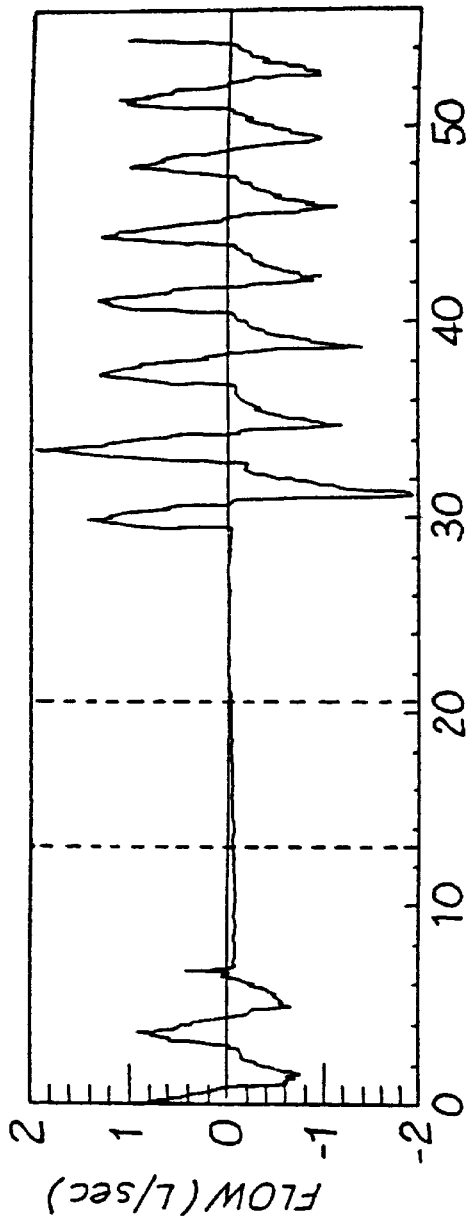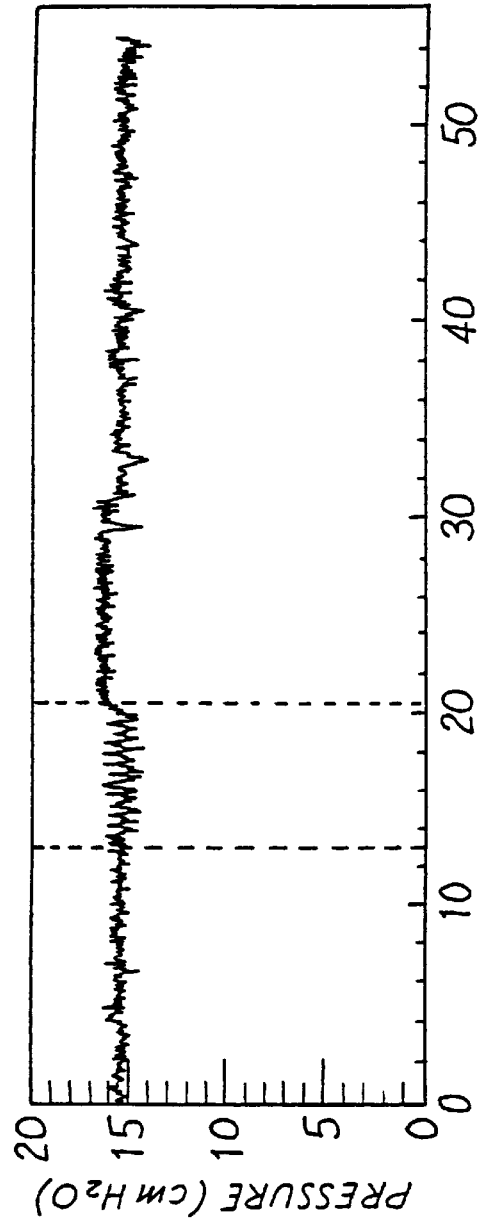

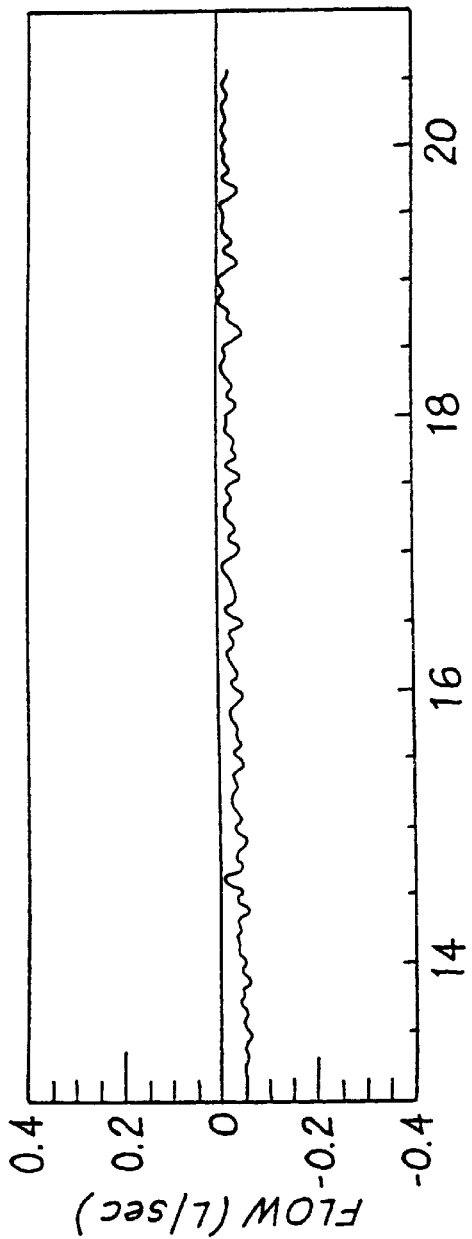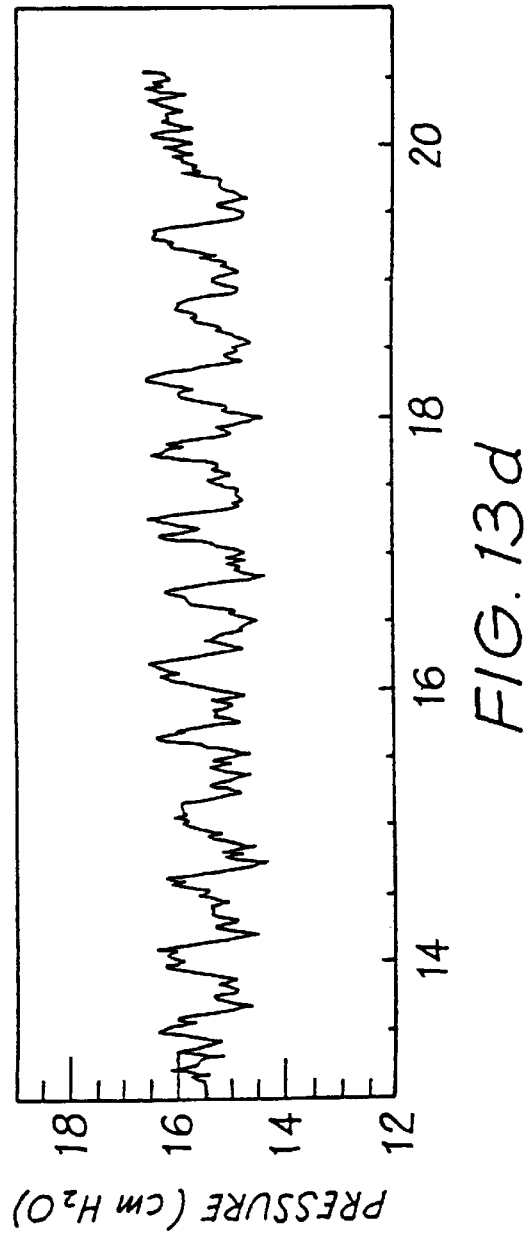

DETERMINATION OF THE OCCURRENCE OF AN APNEA

This application is a continuation of application Ser. No. 08/335,118 filed Nov. 4, 1994, now U.S. Pat. No. 5,740,345, which was allowed on May 13, 1997.

FIELD OF THE INVENTION

This invention relates to the detection of the occurrence of an apnea (i.e. the complete cessation of breathing) and to the determination of airway patency. The condition of patency of the airway is the converse of a total obstruction of the airway. The invention also relates to the detection of partial obstruction of the airway (i.e. obstructed breathing). The detection and monitoring of apneas, airway patency and obstruction is advantageous in the diagnosis and treatment of respiratory conditions that have adverse effects on a person's wellbeing.

The expression "airway" as used herein is to be understood as the anatomical portion of the respiratory system between the nares and the bronchii, including the trachea. The expression "respiration" is to be understood as the continually repeating events of inspiration (inhaling) followed by expiration (exhaling).

BACKGROUND OF THE INVENTION

In the Sleep Apnea syndrome a person stops breathing during sleep. Cessation of airflow for more than 10 seconds is called an "apnea". Apneas lead to decreased blood oxygenation and thus to disruption of sleep. Apneas are traditionally (but confusingly) categorized as either central, where there is no respiratory effort, or obstructive, where there is respiratory effort. With some central apneas, the airway is patent, and the subject is merely not attempting to breathe. Conversely, with other central apneas and all obstructive apneas, the airway is not patent (i.e. occluded). The occlusion is usually at the level of the tongue or soft palate.

The airway may also be partially obstructed (i.e. narrowed or partially patent). This also leads to decreased ventilation (hypopnea), decreased blood oxygenation and disturbed sleep.

The dangers of obstructed breathing during sleep are well known in relation to the Obstructive Sleep Apnea (OSA) syndrome. Apnea, hypopnea and heavy snoring are recognised as causes of sleep disruption and risk factors in certain types of heart disease. More recently it has been found that increased upper airway resistance (Upper Airway Resistance syndrome) during sleep without snoring or sleep apnea also can cause sleep fragmentation and daytime sleepiness. It is possible there is an evolution from upper airway resistance syndrome to sleep apnea, accompanied by a worsening of clinical symptoms and damage to the cardiovascular system.

The common form of treatment of these syndromes is the administering of Continuous Positive Airway Pressure (CPAP). The procedure for administering CPAP treatment has been well documented in both the technical and patent literature. Briefly stated, CPAP treatment acts as a pneumatic splint of the airway by the provision of a positive pressure, usually in the range 4–20 cm $H_2O$. The air is supplied to the airway by a motor driven blower whose outlet passes via an air delivery hose to a nose (or nose and/or mouth) mask sealingly engaged to a patient's face. An exhaust port is provided in the delivery tube proximate to the mask. More sophisticated forms of CPAP, such as bi-level CPAP and autosetting CPAP, are described in U.S. Pat. Nos. 5,148,802 and 5,245,995 respectively.

Various techniques are known for sensing and detecting abnormal breathing patterns indicative of obstructed breathing. U.S. Pat. No. 5,245,995, for example, describes how snoring and abnormal breathing patterns can be detected by inspiration and expiration pressure measurements while sleeping, thereby leading to early indication of preobstructive episodes or other forms of breathing disorder. Particularly, patterns of respiratory parameters are monitored, and CPAP pressure is raised on the detection of predefined patterns to provide increased airway pressure to, ideally, subvert the occurrence of the obstructive episodes and the other forms of breathing disorder.

As noted above, central apneas need not involve an obstruction of the airway, and often occur during very light sleep and also in patients with various cardiac, cerebrovascular and endocrine conditions unrelated to the state of the upper airway. In those cases where the apnea is occurring without obstruction of the airway, there is little benefit in treating the condition by techniques such as CPAP. Also, known automated CPAP systems cannot distinguish central apneas with an open airway from apneas with a closed airway, and may inappropriately seek to increase the CPAP splinting air pressure unnecessarily. Such unnecessary increases in pressure reflexly inhibit breathing, further aggravating the breathing disorder.

Other limitations associated with the prior art include the inability to detect airway patency and the absence of progressive, heirarchic response to increasingly severe indicators of airway obstruction for which the mask pressure should be increased.

It would be useful, however, to even more sensitively and reliably detect the conditions of partial obstruction, as well as apnea and patency, as this would assist in the design of equipment to prevent these conditions from occurring. In a similar way, means for detecting and monitoring mildly obstructed breathing would be useful in diagnosing and treating Upper Airway Resistance syndrome and monitoring that treatment is optimal.

SUMMARY OF THE INVENTION

In accordance with a first aspect the invention discloses a method for determining the occurrence of an apnea in a patient, the method comprising the steps of:

measuring respiratory air flow from the patient as a function of time;

determining the variance of said measured air flow; and determining from said variance that an apnea is occurring.

The variance can be a moving average over the time window. Further, there can be a further step of comparing the variance with a threshold value, and if the variance falls below the threshold value then an apnea is occurring. The measured air flow can be expressed as an air flow signal. Advantageously, the respiratory air flow is sampled at equally spaced points in time to give a sampled air flow signal. Further, it can be the case that the variance must fall below the threshold value for a predetermined period of time before it is determined that an apnea is occurring. Advantageously the method can comprise the further step of either commencing continuous positive airway pressure (CPAP) treatment or increasing CPAP treatment pressure to the patient if an apnea is occurring.

In accordance with a further aspect the invention discloses a method for detecting partial obstruction of the airway of a patient, the method comprising the steps of:

measuring respiratory air flow from the patient;

detecting the inspiratory part of said air flow;

normalising said inspiratory part; and determining an index value of a mid-portion of said normalised inspiratory part as a measure of partial obstruction.

Conveniently, the index value is determined from the amplitude of the mid-portion of the normalised inspiratory part. The index value can be determined as the arithmetic mean value of the amplitude in the mid-portion. Alternatively, the index value is determined from the flatness of the mid-portion. Yet further, the index value can be determined as the root mean square (RMS) deviation of the normalised inspiratory part in the mid-portion with respect to unity. The RMS deviation can be compared against a threshold value to determine the degree of obstruction. Still further, the step of normalising can include scaling the inspiratory part to unity duration and unity area. The determination also can be performed over a plurality of inspiratory events. In this way a moving mean value of amplitude or a moving RMS deviation can be formed. The respiratory air flow also can be sampled at spaced instants in time. Advantageously there is the further step of either commencing CPAP treatment or increasing CPAP treatment pressure to the patient if there is partial obstruction of the airway.

The invention yet further discloses a method for determining the degree of obstruction of the airway of a patient receiving continuous positive airway pressure (CPAP) treatment by apparatus for supplying CPAP to the patient's airway, the method comprising the steps of:

measuring respiratory air flow from the patient to give an air flow signal;

filtering said air flow signal to reject components at least due to respiration to give a filtered air flow signal having components due to patient snoring and noise of said CPAP apparatus;

predicting a CPAP apparatus noise component of said filtered air flow signal; and subtracting said predicted noise component from said filtered air flow signal to give a snore component signal as a measure of the degree of obstruction of the airway.

In a preferred form, the filtering step includes bandpass filtering also to reject high frequency noise components.

The invention yet further discloses a method for determining patency of the airway of a patient, the method comprising the steps of:

applying an oscillatory pressure waveform of known frequency to the patient's airway;

measuring respiratory air flow from the patient; and determining that the airway is patent if there is a component of said air flow at said known frequency induced by said oscillatory pressure waveform.

Advantageously the air flow component is determined from the amplitude of the air flow signal, and there is the further step of comparing the magnitude with a threshold value and if the magnitude is greater than the threshold value then the airway is declared patent. Furthermore, the method can be performed when the patient is having an apnea and there is zero air flow. The step of determining can be said to identify modulation of the measured air flow by the oscillatory pressure waveform.

The invention yet further discloses a method for determining the degree of patency of the airway of a patient, the method comprising the steps of:

applying an oscillatory pressure waveform of known frequency and magnitude at an entrance to the patient's airway;

measuring respiratory air flow from the patient;

determining the magnitude of the component of said air flow at said known frequency induced by said oscillatory pressure waveform; and determining the degree of patency as the ratio of said induced air flow magnitude and said oscillatory pressure waveform magnitude.

The measured air flow can be expressed as an air flow signal. Furthermore, the method can be performed when the patient is asleep, and further advantageously, when it previously has been determined that the patient is having an apnea. In the case of an apnea there is zero air flow.

The invention yet further discloses a method for determining patency of the airway of a patient, the method comprising the steps of:

measuring respiratory air flow from the patient;

analysing said air flow to detect the presence of cardiogenic air flow, and if said cardiogenic air flow is present then the airway is declared patent.

Again, the measured air flow can be expressed as an air flow signal. The respiratory air flow can be high pass filtered to reject components due to respiration. Further, the step of analysing detects the presence of a periodic component. The periodic component can include a fundamental component together with a sub-multiple or harmonic thereof. The step of analysing can further include performing a Fourier transformation on the air flow signal. Conveniently there can be the further step of detecting the patient's cardiac rate, and whereby the analysing step includes detecting a component of the air flow at the cardiac rate. Furthermore, the method can be performed when the patient is having an apnea and there is zero air flow.

The invention yet further discloses a method for controlling the administration of CPAP treatment to the airway of a patient by means controllable to supply breathable air to the patient's airway continually at a selectable pressure elevated above atmospheric pressure, the method comprising the step of:

commencing or increasing CPAP treatment pressure if:
(a) an apnea is occurring, determined by the steps of:
measuring respiratory air flow from the patient as a function of time; and determining the variance of said measured air flow as an indication of an apnea occurring;
or (b) there is partial obstruction of the airway, determined by the steps of:
measuring respiratory air flow from the patient;
detecting the inspiratory part of said air flow;
normalising said inspiratory part; and
determining an index value of a mid-portion of said normalised inspiratory part as a measure of partial obstruction;
or (c) there is patency of the airway, determined by the steps of:
(i) applying an oscillatory pressure waveform of known frequency to the patient's airway;
measuring respiratory air flow from the patient; and
determining that the airway is patent if there is a component of said air flow at said known frequency induced by said oscillatory pressure waveform;
or (ii) measuring respiratory air flow from the patient; and
analysing said measured air flow to detect the presence of cardiogenic air flow, and if so then the airway is declared patent.

The invention yet further discloses apparatus for determining the occurrence of an apnea in a patient, the apparatus comprising:

means for measuring respiratory air flow from the patient as a function of time;

means for determining the variance of said measured air flow; and means for determining from said variance that an apnea is occurring.

The invention yet further discloses apparatus for detecting partial obstruction of the airway of a patient, the apparatus comprising:

means for measuring respiratory air flow from the patient;

means for detecting the inspiratory part of said air flow;

means for normalising said inspiratory part; and means for determining an index value of a mid-portion of said normalised inspiratory part as a measure of partial obstruction.

The invention yet further discloses apparatus for determining the degree of obstruction of the airway of a patient receiving continuous positive airway pressure (CPAP) treatment by means for supplying CPAP to the patient's airway, the apparatus comprising:

means for measuring respiratory air flow from the patient to give an air flow signal;

means for filtering said air flow signal to reject components at least due to respiration to give a filtered air flow signal having components due to patient snoring and noise of said CPAP apparatus;

means for predicting a CPAP apparatus noise component of said filtered air flow signal; and means for subtracting said predicted noise component from said filtered air flow signal to give a snore component signal as a measure of the degree of obstruction of the airway.

The invention yet further discloses apparatus for determining patency of the airway of a patient, the apparatus comprising:

means for applying an oscillatory pressure waveform of known frequency to the patient's airway;

means for measuring respiratory air flow from the patient; and means for determining that the airway is patent if there is a component of said air flow at said known frequency induced by said oscillatory pressure waveform.

The invention yet further discloses apparatus for determining the degree of patency of the airway of a patient, the apparatus comprising:

means for applying an oscillatory pressure waveform of known frequency and magnitude to the patient's airway;

means for measuring respiratory air flow from the patient;

means for determining the magnitude of the component of said air flow at said known frequency induced by said oscillatory pressure waveform; and means for determining the degree of patency as the ratio of said induced air flow magnitude and said oscillatory pressure waveform magnitude.

The invention yet further discloses apparatus for determining patency of the airway of a patient, the apparatus comprising:

means for measuring respiratory air flow from the patient; and means for analysing said measured air flow to detect the presence of cardiogenic air flow, and if said cardiogenic air flow is present then the airway is declared patent.

The invention yet further discloses apparatus for controlling the administration of CPAP treatment to the airway of a patient comprising:

means controllable to supply breathable air to the patient's airway continually at a selectable pressure elevated above atmospheric pressure;

controlling means for commencing or increasing CPAP treatment pressure if:

(a) an apnea is occurring, determined by:

measuring respiratory air flow from the patient as a function of time; and determining the variance of said measured air flow as an indication of an apnea occurring;

or (b) there is partial obstruction of the airway, determined by:

measuring respiratory air flow from the patient;

detecting the inspiratory part of said air flow;

normalising said inspiratory part; and determining an index value of a mid-portion of said normalised inspiratory part as a measure of partial obstruction;

or (c) there is patency of the airway, determined by:

(i) applying an oscillatory pressure waveform of known frequency to the patient's airway;

measuring respiratory air flow from the patient; and determining that the airway is patent if there is a component of said air flow at said known frequency induced by said oscillatory pressure waveform;

or (ii) measuring respiratory air flow from the patient; and analysing said measured air flow to detect the presence of cardiogenic air flow, and if so then the airway is declared patent.

BRIEF DESCRIPTION OF THE DRAWINGS

Embodiments of the invention will now be described with reference to the accompanying drawings, in which:

FIGS. 12a–12d and 13a–13d show graphs of clinical respiratory data demonstrating the detection of patency;

DETAILED DESCRIPTION OF PREFERRED EMBODIMENTS

Figure 1:
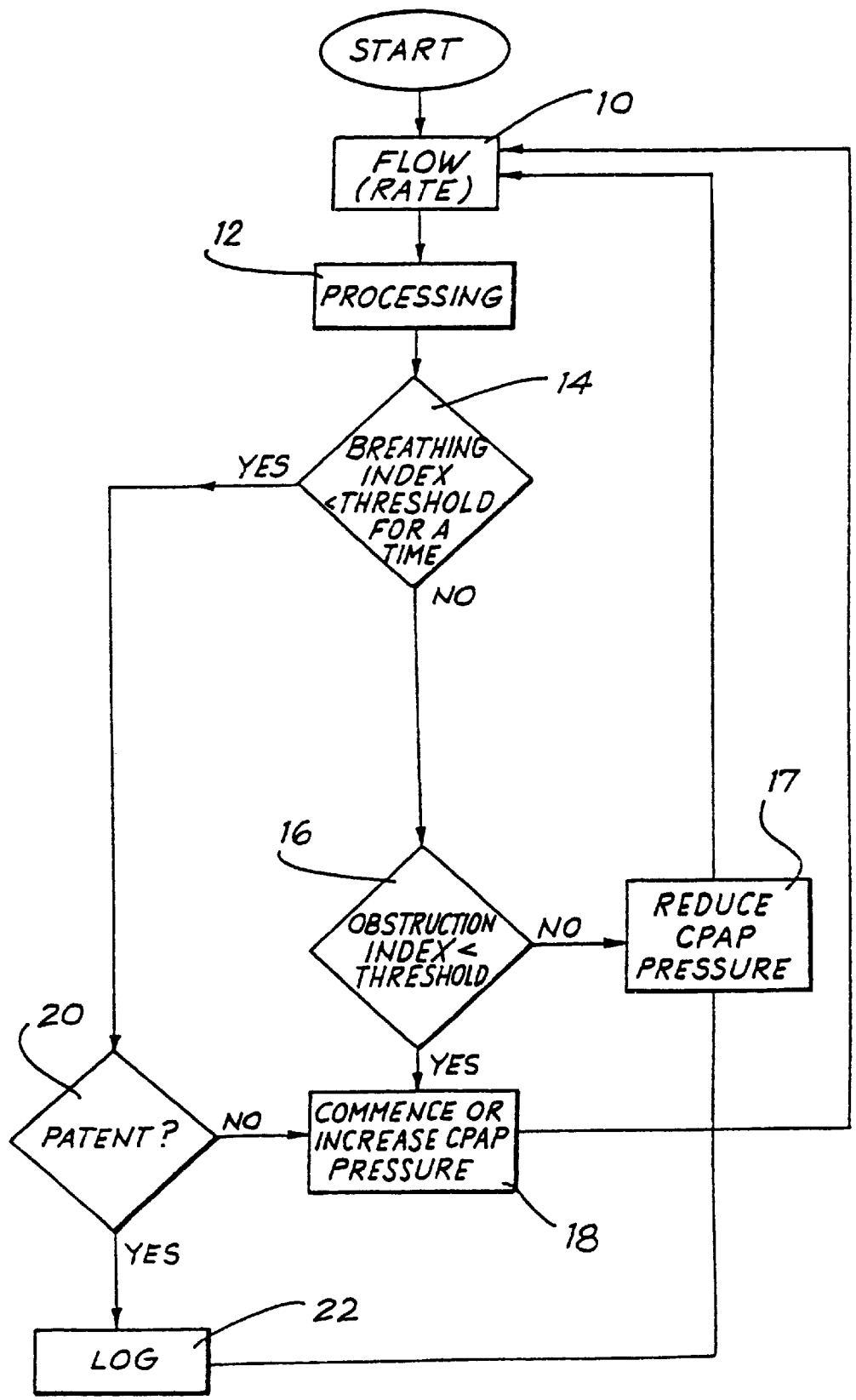
FIG. 1 shows a flow diagram of the basic methodology of an embodiment.

FIG. 1 is a flow diagram of the basic methodology of one embodiment. The first step 10 is the measurement of respiratory flow (rate) over time. This information is processed in step 12 to generate Index values to be used as qualitative measures for subsequent processing. Step 14 detects whether an apnea is occurring by comparison of the Breathing Index with a Threshold value.

If the answer in step 14 is "Yes", an apnea is in progress and there then follows a determination of patency in step 20. If there is patency of the airway, a central apnea with an open airway is occurring, and, if desired, the event is logged in step 22. If the result of step 20 is that the airway is not patent, then a total obstructive apnea or a central apnea with closed airway is occurring, which results in the commencement or increase in CPAP treatment pressure in step 18. If desired, step 18 may include the optional logging of the detected abnormality.

If the answer in step 14 is "No", the Obstruction Index is compared with another Threshold value in step 16, by which the determination of obstruction of the airway is obtained. If "Yes" in step 16, then there is a partial obstruction, and if "No", there is no obstruction (normalcy).

Thus step 18 applies in the case of a complete or partial obstruction of the airway with a consequential increase in CPAP treatment pressure. In the instance of a central apnea with patent airway (steps 20,22) or normal breathing with no obstruction, the CPAP treatment pressure rather is reduced, in accordance with usual methodologies that seek to set the minimal pressure required to obviate, or at least reduce, the occurrence of apneas. The amount of reduction in step 17 may, if desired, be zero.

The methodology represented in FIG. 1 is of a clinical embodiment, where patient CPAP pressure is controlled over time as appropriate. A purely diagnostic embodiment operates in the same manner except it omits the CPAP pressure increase and pressure decrease actions of step 18 and step 17 respectively.

Figure 2:
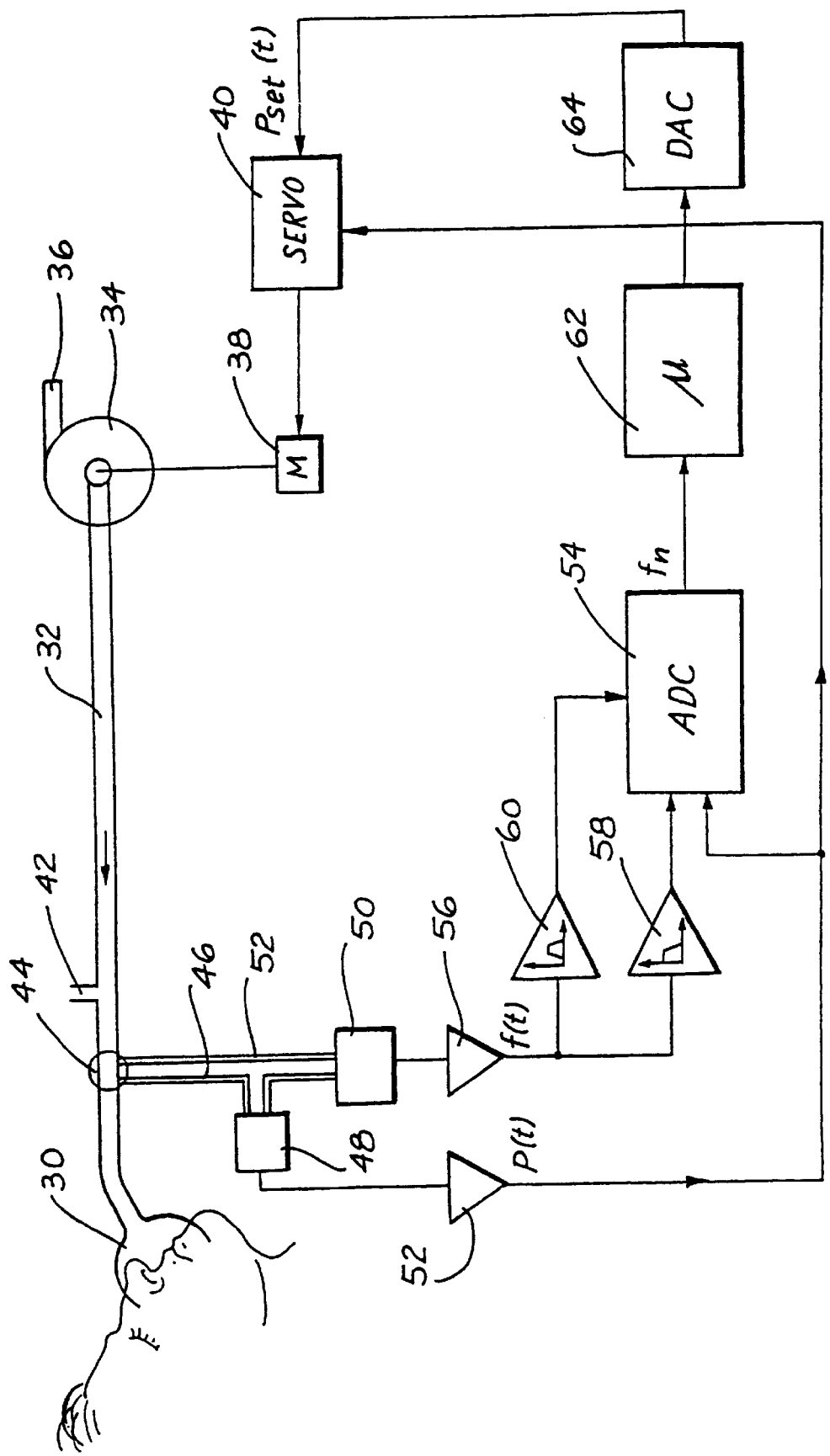
FIG. 2 shows, in diagrammatic form, apparatus embodying the invention.

FIG. 2 shows, in diagrammatic form, clinical CPAP apparatus in accordance with one embodiment for implementing the methodology of FIG. 1. A mask 30, whether either a nose mask and/or a face mask, is sealingly fitted to a patient's face. Fresh air, or oxygen enriched air, enters the mask 30 by flexible tubing 32 which, in turn, is connected with a motor driven turbine 34 to which there is provided an air inlet 36. The motor 38 for the turbine is controlled by a motor-servo unit 40 to either increase or decrease the pressure of air supplied to the mask 30 as CPAP treatment. The mask 30 also includes an exhaust port 42 that is close to the junction of the tubing 34 with the mask 30.

Interposed between the mask 30 and the exhaust 42 is a flow-resistive element 44. This can take the form of an iris across which a differential pressure exits. The mask side of the flow-resistive element 44 is connected by a small bore tube 46 to a mask pressure transducer 48 and to an input of a differential pressure transducer 50. Pressure at the other side of the flow-resistive element 44 is conveyed to the other input of the differential pressure transducer 50 by another small bore tube 52.

The mask pressure transducer 48 generates an electrical signal in proportion to the mask pressure, which is amplified by amplifier 52 and passed both to a multiplexer/ADC unit 54 and to the motor-servo unit 40. The function of the signal provided to the motor-servo unit 40 is as a form of feedback to ensure that the actual mask static pressure is controlled to be closely approximate to the set point pressure.

The differential pressure sensed across the flow-resistive element 44 is output as an electrical signal from the differential pressure transducer 50, and amplified by another amplifier 56. The output signal from the amplifier 56 therefore represents a measure of the mask or respiratory airflow rate. A large dynamic range can be achieved by using a flexible-vaned iris as the flow-resistive element 44.

The output signal from the amplifier 56 is low-pass filtered by the low-pass filter 58, typically with an upper limit of 10 Hz. The amplifier 56 output signal is also bandpassed by the bandpass filter 60, and typically in a range of 30–300 Hz. The outputs from both the low-pass filter 58 and the bandpass filter 60 are provided to the multiplexer/ADC unit 54. The multiplexed and digitized output from the multiplexer/ADC unit 54 is, in turn, passed to a controller 62, typically constituted by a micro-processor based device also provided with program memory and data processing storage memory. A component of the multiplexed output is a digitized and manipulated form of the air flow signal f(t), represented as $f_n$.

Dependant upon the specific processing functions it performs, the controller 62 outputs a pressure request signal which is converted by a DAC 64, and passed to the motor-servo unit 40. This signal therefore represents the set point pressure ($P_{set}(t)$) to be supplied by the turbine 34 to the mask 30 in the administration of CPAP treatment.

The controller 62 is programmed to perform a number of processing functions, as presently will be described.

As an alternative to the mask pressure transducer 48, a direct pressure/electrical solid state transducer (not shown) can be mounted from the mask with access to the space therewithin, or to the air delivery tubing 32 proximate the point of entry to the mask 30.

Figure 3:
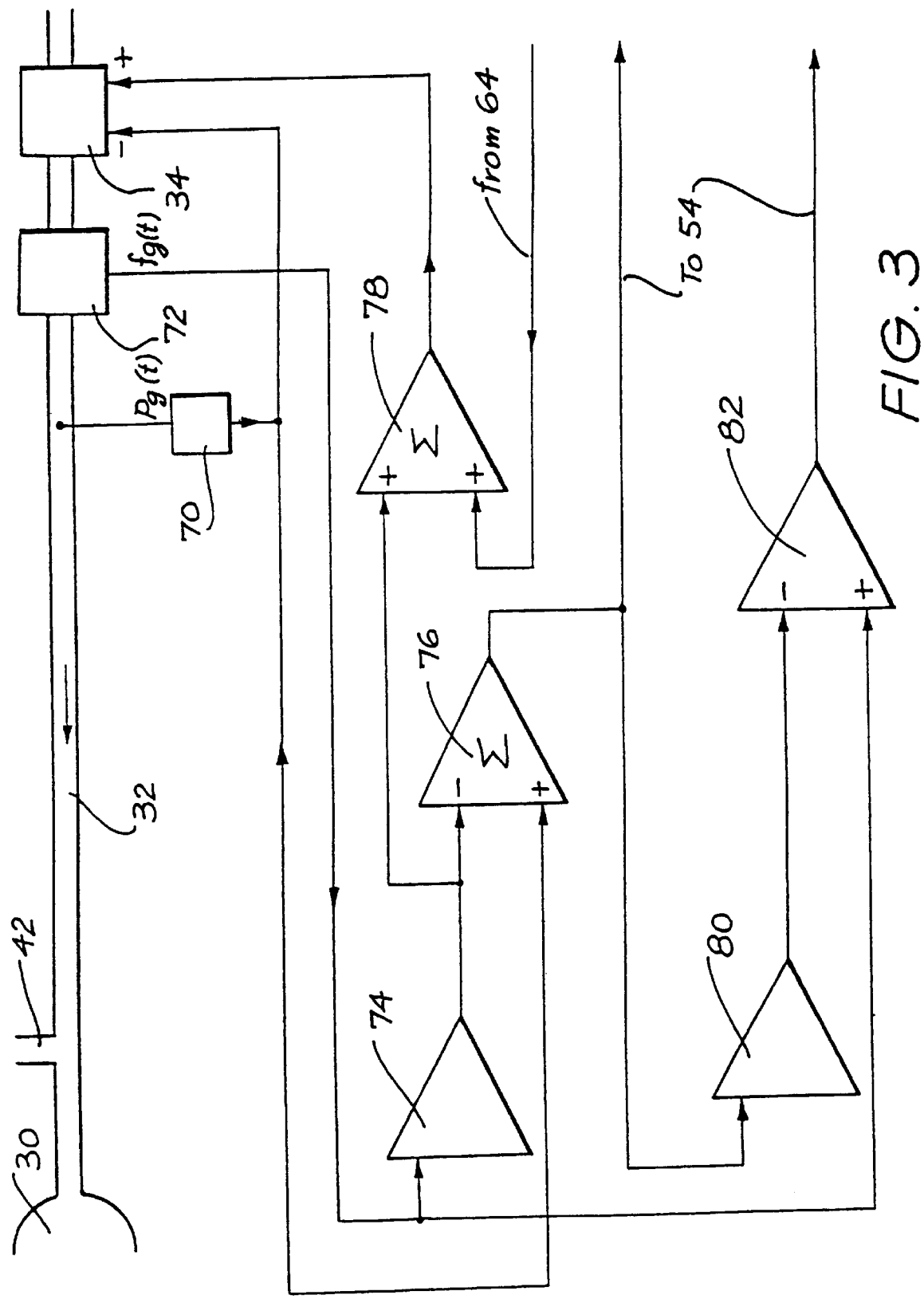
FIG. 3 shows an alternative arrangement of the apparatus of FIG. 2.

Further, it may not be convenient to mount the flow transducer 44 at or near the mask 30, nor to measure the mask pressure at or near the mask. An alternative arrangement, where the flow and pressure transducers are mounted at or near the air pressure generator (in the embodiment being the turbine 34) is shown in FIG. 3.

The pressure $p_g(t)$ occurring at the pressure generator 34 outlet is measured by a pressure transducer 70. The flow $f_g(t)$ through tubing 32 is measured with flow sensor 72 provided at the output of the turbine 34.

The pressure loss along tubing 32 is calculated in step 74 from the flow through the tube $f_g(t)$, and a knowledge of the pressure-flow characteristic of the tubing, for example by table lookup.

The pressure at the mask $p_m$ is then calculated in subtraction step 76 by subtracting the tube pressure loss from $p_g(t)$.

The pressure loss along tube 32 is then added to the desired set pressure at the mask $p_{set}(t)$ in summation step 78 to yield the desired instantaneous pressure at the pressure generator 34. Preferably, controller of the pressure generator 34 has a negative feedback input from the pressure transducer 70, so that the desired pressure from step 78 is achieved more accurately.

The flow through the exhaust 42 is calculated from the pressure at the mask (calculated in step 76) from the pressure-flow characteristic of the exhaust step 80, for example by table lookup.

Finally, the mask flow is calculated by subtracting the flow through the exhaust 42 from the flow through the tubing 32, in subtraction step 82.

The methodology put into place by the controller 62 will now be described with reference to the apparatus of FIG. 2.

A. Determination of Apnea

This section generally corresponds to steps 10, 12, and 14 as shown in FIG. 1.

Figure 4:
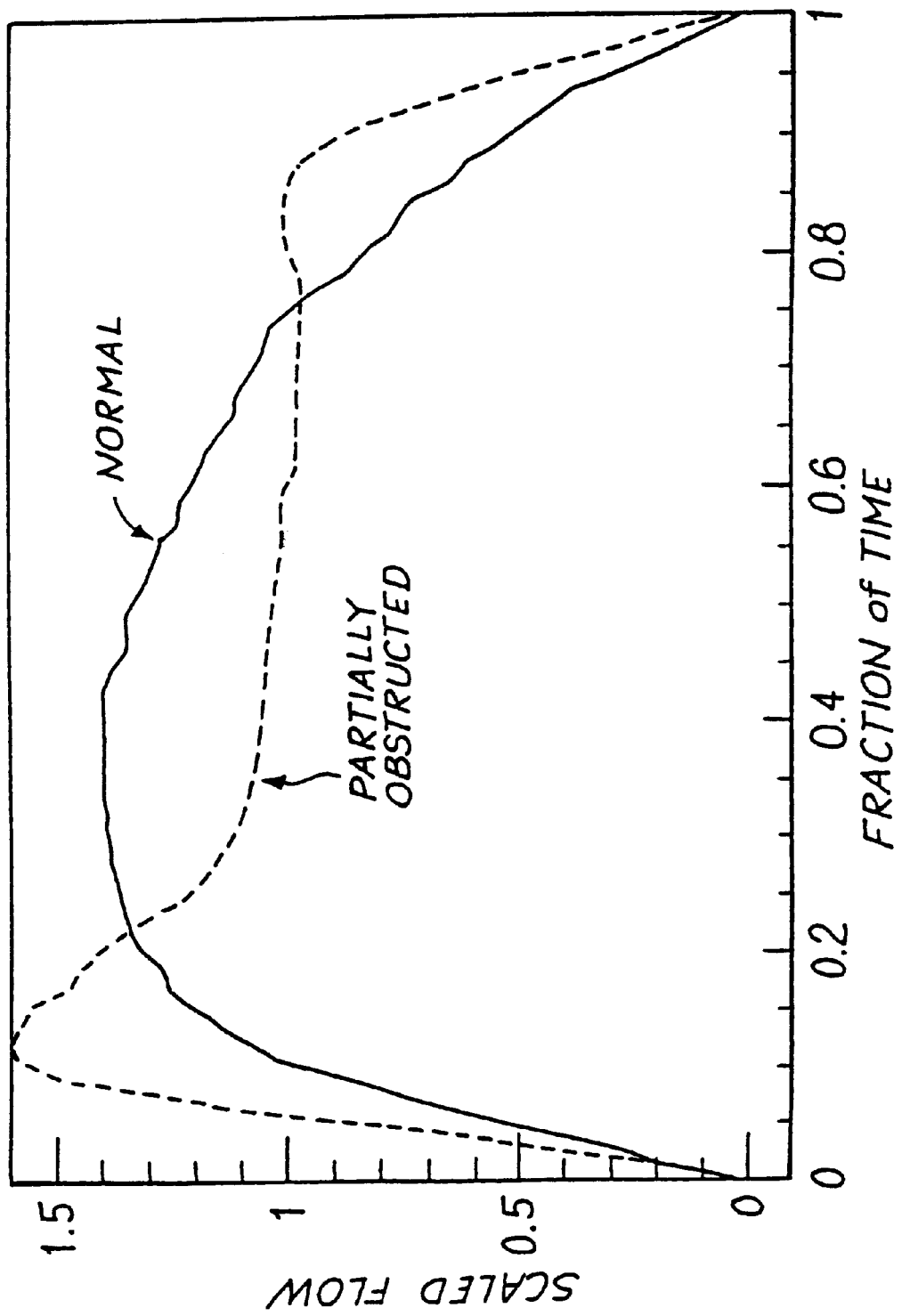
FIG. 4 shows a graph of air flow with time for normal and partially obstructed inspiration.

Partial upper airway obstruction in untreated or partially treated Obstructive Sleep Apnea syndrome, and the related High Airway Resistance syndrome, leads to mid-inspiratory flow limitation, as shown in FIG. 4, which shows typical inspiratory waveforms respectively for normal and partially obstructed breaths.

As discussed previously, the respiratory air flow is determined by means of the differential pressure transducer 48, and a signal representing the air flow is continuously digitized and passed to the controller 62. If necessary, the controller 62 can linearise the flow signal, for example, by a table lookup. Occasionally, complete obstruction of the airway can occur unexpectedly, for example in a previously untreated patient, without a period of preceding partial obstruction. Consequently, the processing steps 12,14 shown in FIG. 1 also detect the presence of complete or near-complete cessation of air flow, or apnea, using the measure of the Breathing Index in step 14.

Figure 5:
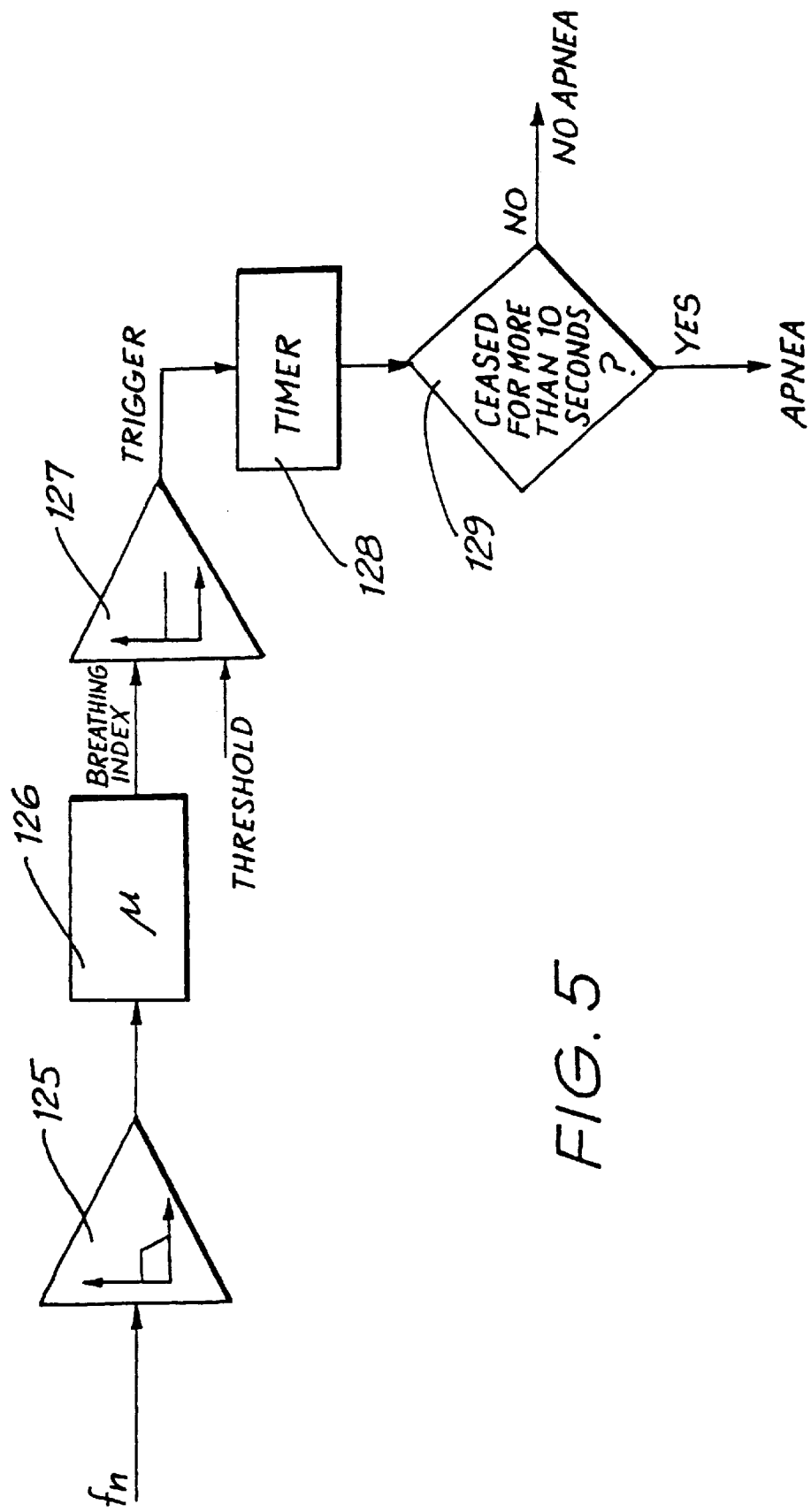
FIG. 5 shows a flow diagram of the determination of an apnea.

This is achieved, for example as shown in FIG. 5, by low-pass filtering of the mask air flow signal $f_n$ by low-pass filter element 125, typically with a 1 Hz cutoff, and calculating the moving average variance by the computational block 126.

The Breathing Index at any given point in time is calculated as the square root of the variance of the digitized flow signal, $f_n$:

$$\text{breathing index} = \sqrt{\frac{\sum_{i=0}^{I-1} f_{n-i}^2 - \frac{1}{I}\left(\sum_{i=0}^{I-1} f_{n-i}\right)^2}{I}}$$

where $I = 2 \cdot \text{sample rate}$

The average variance calculated over a moving time window is compared with a Threshold by the level detector 127, to generate an "airflow-ceased" trigger. This starts the timer 128. If the trigger persists for more than 10 seconds, the comparator 129 declares an apnea. The Threshold may be a fixed value, typically 0.1 l/sec, or may be a chosen percentage (typically 10 or 20%) of the average ventilation over the last several minutes (typically 5 minutes). For convenience, instead of comparing the Threshold with the square root of the variance, one can square the Threshold, and compare with the variance directly.

Conversely, if airflow resumes before 10 seconds lapses, the timer 128 is reset and no apnea is declared. If an apnea is taking place, the patency of the airway must also be determined as an indicator of whether the apnea is of the central type with open airway, or otherwise. The processing performed by the controller 62 to achieve this determination will be discussed presently.

The method can, of course, be used instantaneously without requiring the elapse of a time interval before an apnea is declared.

The method is advantageous in comparison with known methods for detecting apnea, such as single zero crossing methods, because it is relatively insensitive to leaks. Furthermore, apneas are still detected in the presence of cardiogenic, as opposed to respiratory, air flow.

B. Determination of Airway Obstruction

The Obstruction Index is calculated in step 12. Either of two alternate Obstruction indices can be calculated. These will be referred to as shape factor 1 and shape factor 2.

The Obstruction Index is then compared with a threshold in step 16 of FIG. 1. If the obstruction Index is less than the threshold value, CPAP treatment pressure is increased in step 18. Otherwise, the CPAP pressure may be reduced in optional step 17.

Figure 6A:
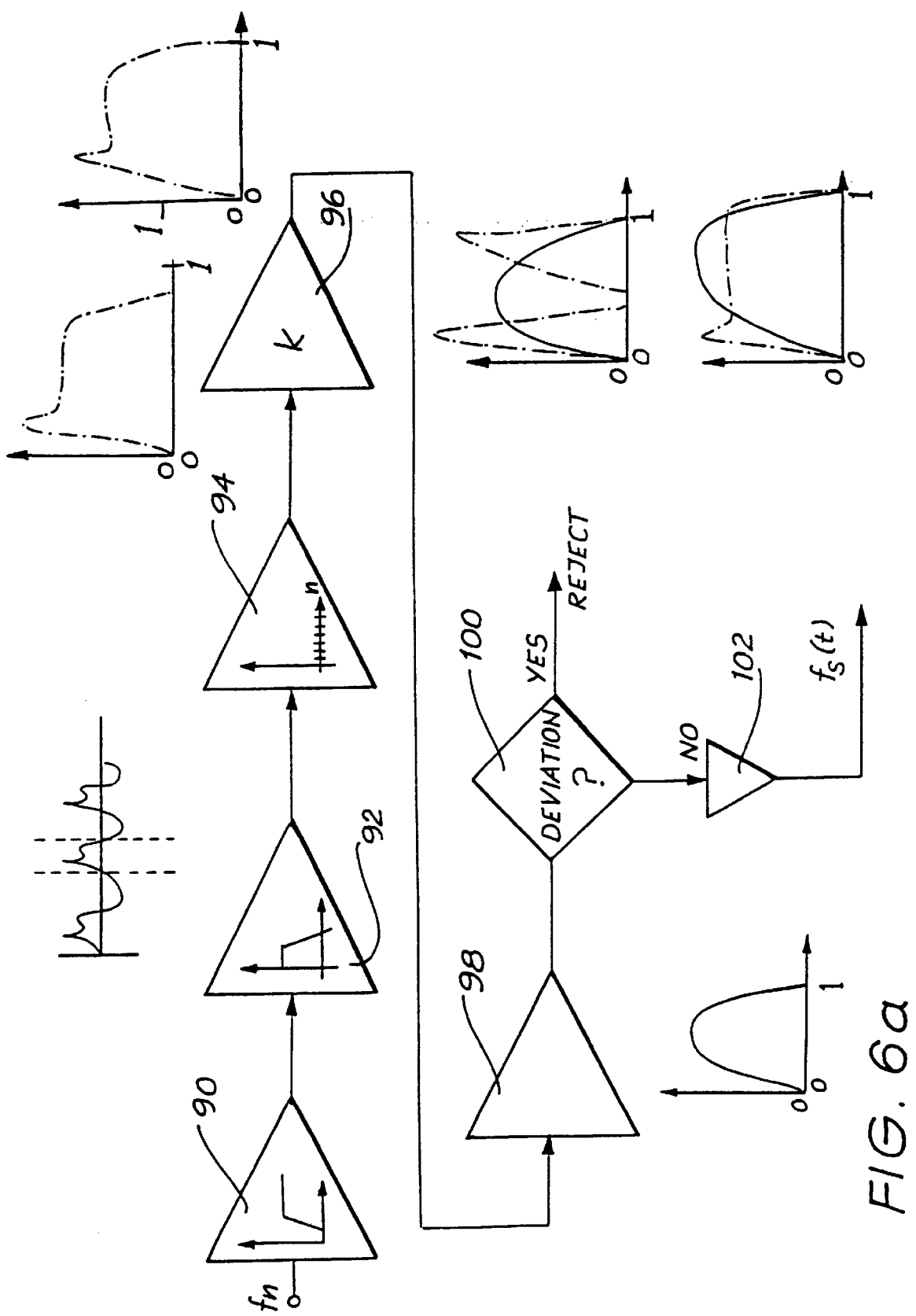
FIGS. 6a and 6b show a flow diagram of the calculation of the shape factors.

As shown in FIG. 6*a*, the digitized airflow signal, $f_n$, has any components below 0.1 Hz due to leaks of the mask 30 subtracted by a high-pass filter 90. The inspiratory and expiratory portions of each breath are then identified by a zero-crossing detector 92. A number of evenly spaced points (typically sixty-five), representing points in time, are interpolated by an interpolator 94 along the inspiratory flow-time curve for each breath. The curve described by the points is then scaled by a scaler 96 to have unity length (duration/period) and unity area to remove the effects of changing respiratory rate and depth.

Conveniently, the scaled breaths are compared in a comparator 98 with a pre-stored template representing a normal unobstructed breath. The template is very similar to the curve for a normal inspiratory event as shown in FIG. 4. Breaths deviating by more than a specified threshold (typically 1 scaled unit) at any time during the inspiration from this template, such as those due to coughs, sighs, swallows and hiccups, as determined by the test element 100, are rejected.

For data for which the test is satisfied, a moving average of the first such scaled point is calculated by the arithmetic processor 102 for the preceding several inspiratory events. This is repeated over the same inspiratory events for the second such point, and so on. Thus, sixty five scaled data points are generated by the arithmetic processor 102, and represent a moving average of the preceding several inspiratory events. The moving average of continuously updated values of the sixty five points are hereinafter called the "scaled flow", designated as $f_s(t)$. Equally, a single inspiratory event can be utilised rather than a moving average.

From the scaled flow two shape factors that directly relate to the determination of partial obstruction are calculated. Each shape factor equates to the Obstruction Index discussed above.

Shape factor 1 is the ratio of the mean of the middle thirty-three scaled flow points to the mean overall sixty-five scaled flow points. This is thus a determination of the reduction of the magnitude (depression) of the mid-portion of the scaled inspiratory event(s). Since the mean for all sixty five points is unity, the division need not actually be performed.

$$\text{shape factor 1} = \frac{\frac{1}{33}\sum_{t=16}^{48} f_s(t)}{\frac{1}{65}\sum_{t=1}^{65} f_s(t)}$$

which reduces simply to $$\frac{1}{33}\sum_{t=16}^{48} f_s(t)$$

For a normal inspiratory event this ratio will have an average value in excess of unity, because a normal such inspiratory event is of higher flow in the middle than elsewhere, as can be seen from FIG. 4. Conversely, for a severely flow-limited breath. the ratio will be unity or less, because flow limitation occurs particularly during the middle half of the breath when the upper airway suction collapsing pressure is maximal. A ratio of 1.17 is taken as the Threshold value (step 16 of FIG. 1) between partially obstructed and unobstructed breathing, and equates to a degree of obstruction that would permit maintenance of adequate oxygenation in a typical user.

In other embodiments the number of sampled points, number of breaths and number of middle points can be varied, and still achieve a meaningful determination of whether partial obstruction is occurring. The Threshold value similarly can be a value other than 1.17.

Alternatively, the second shape factor is calculated as the RMS deviation from unit scaled flow, taken over the middle thirty two points. This is essentially a measure of the flatness of the mid-portion of the scaled respiratory event(s). Expressed mathematically, this is:

$$\text{shape factor } 2 = \sqrt{\frac{\sum_{t=16}^{48} (f_s(t) - 1)^2}{32}}$$

For a totally flow-limited breath, the flow amplitude vs. time curve would be a square wave and the RMS deviation would be zero. For a normal breath, the RMS deviation is approximately 0.2 units, and this deviation decreases as the flow limitation becomes more severe. A threshold value of 0.15 units is used in step 16 of FIG. 1.

Both shape factors discussed above can be utilised independently in implementing the methodology carried by the apparatus of FIG. 2, and result in the sensitive and reliable detection of partially obstructed breathing. Better performance again is obtained by implementing both shape factors executed by the controller 62 so that both shape parameters act together. In this case, shape factor 2 is preferred for use to detect all but the most severe obstructions, and shape factor 1 therefore is preferred for detecting only the most severe obstructions, achieved by reducing the critical threshold from 1.17 to 1.0.

Figure 6B:
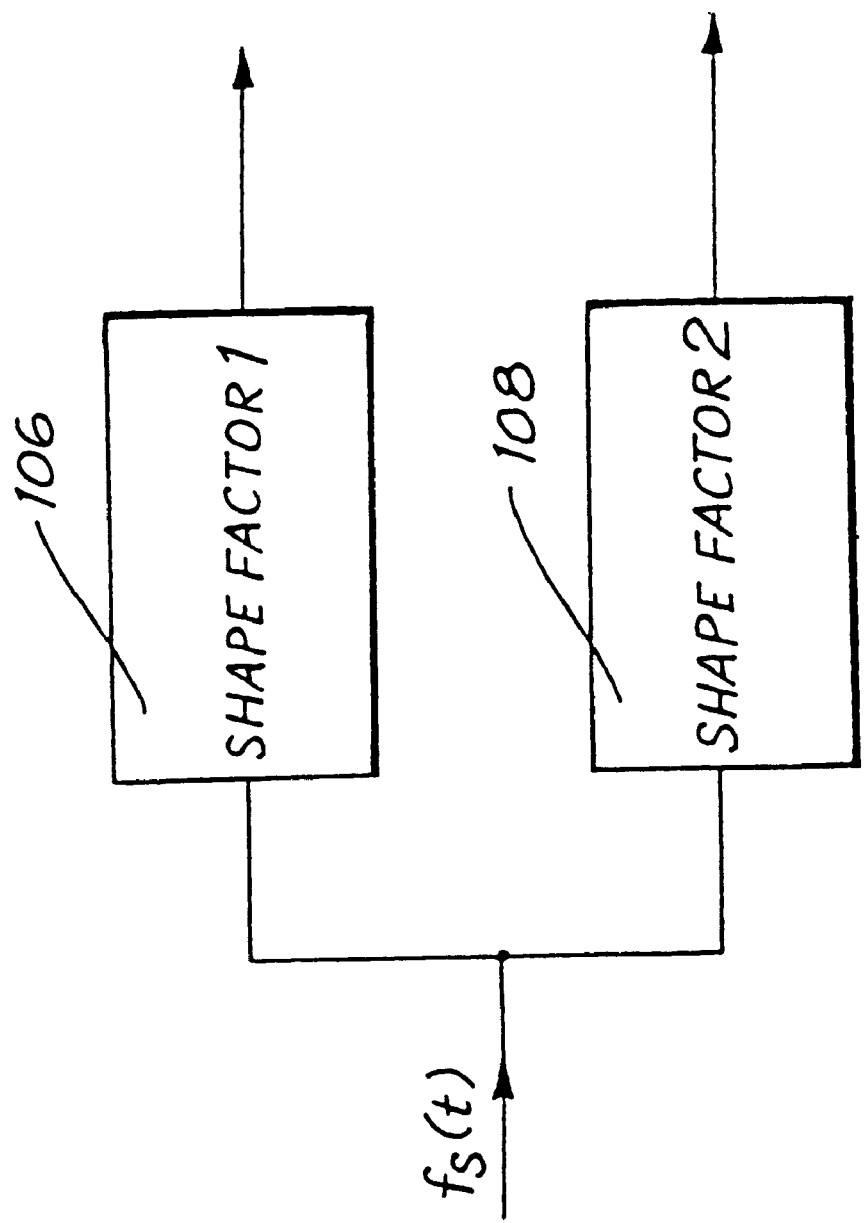
Figure 7:
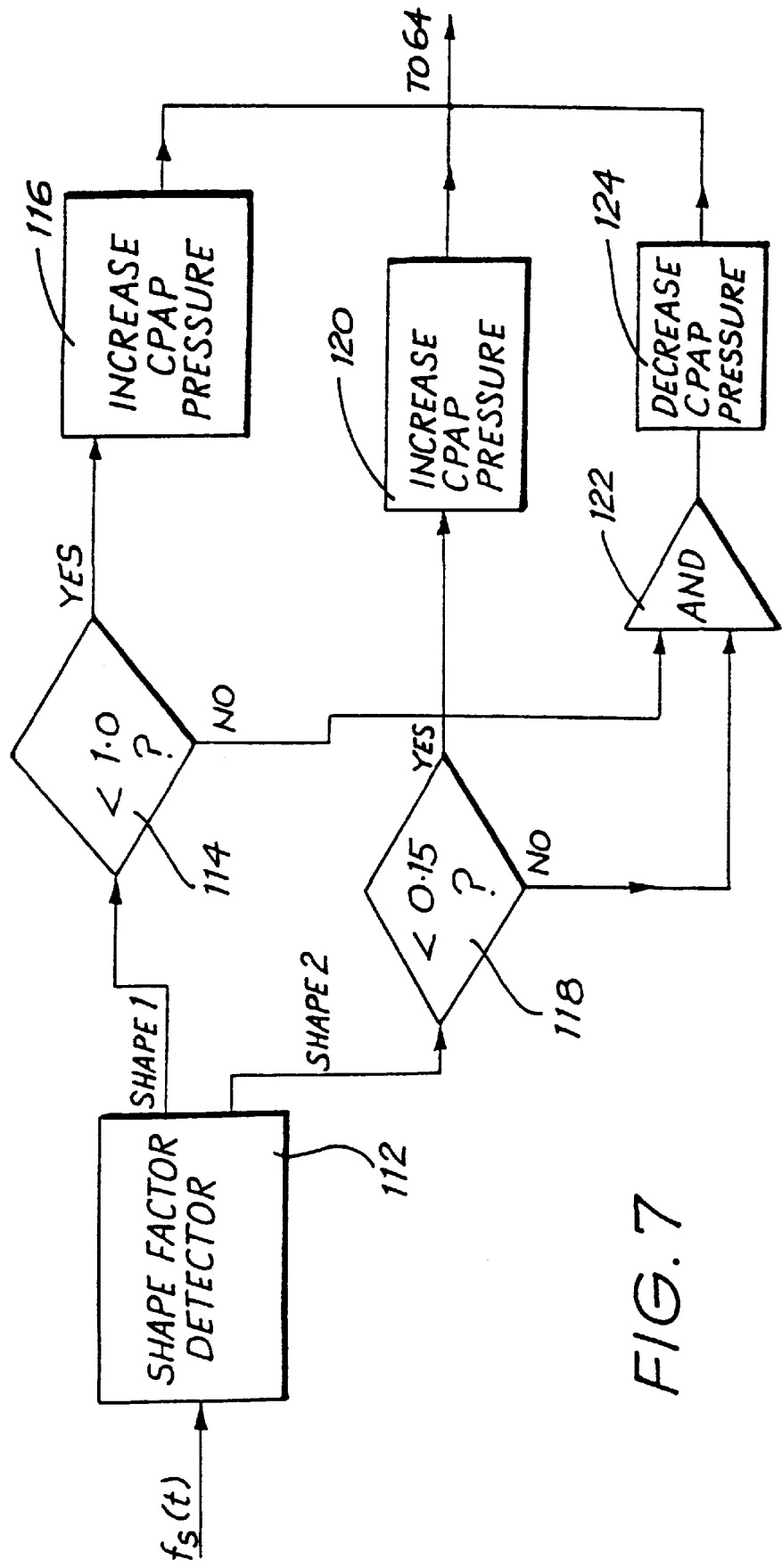
FIG. 7 shows a flow diagram of an embodiment utilising both shape factor methodologies.

FIG. 7 is a flow diagram illustrating the principle of the two shape factors operating in concert. The scaled flow signal $f_s(t)$ is provided to a shape detector 112, such as has been described with reference to FIGS. 6*a* and 6*b*. The shape detector 112 generates shape factor 1 and shape factor 2. Shape factor 1 is applied to a decision block 114 and compared against the Threshold value of 1.0. If the outcome of the comparison is "Yes", then it is determined that there should be an increase in the CPAP pressure setting, as indicated in block 116. The shape factor 2 is provided to the decision block 118, and a comparison made against the Threshold value of 0.15. If the answer is "Yes", then it also is appropriate for an increase in the CPAP pressure, as shown in block 120.

In either case, if the results of the comparison is "No", then those results are ANDed in the AND gate 122. That is, an output will only be achieved if both Threshold criteria are not satisfied. In this case, there is no partial obstruction, or partial obstruction has subsided, in which case, as indicated in block 124, it is appropriate to decrease the CPAP pressure.

This arrangement avoids any peculiarities affecting either algorithm. For example, the presence of an initial non-flow-limited period early in a breath can permit an early sharp peak in the flow-time curve. This means that the scaled flow during the middle half of the breath may be below unity. For very severely obstructive breaths, the RMS deviation from unity may therefore rise again, and shape factor 2 will fail to recognise such breaths. They will, however, be correctly identified by the now desensitized shape factor 1. Some normal breaths can involve an inspiratory flow-time waveform approximating a right triangle, where the mean flow during the middle half of the inspiration is close to unity. Such a waveform correctly triggers neither shape factor 1 nor shape factor 2. That is, the instantaneous flow during the middle half of the inspiration is only unity at a single point, and above or below unity elsewhere, so the RMS deviation from unit scaled flow will be large.

In summary, the shape factors provide an Index of the state of the airway. They provide a sensitive warning of an airway becoming unstable, and allow early CPAP treatment to occur. Continuing calculation of the moving average shape, and thus the shape factors, provides an accurate on-going assessment of the degree of any such apnea that is not subverted by CPAP treatment in order that modified appropriate treatment or corrective action can be taken.

The shape factors discussed above provide the most sensitive indication of upper airway stability, and therefore result in the smallest increase in the CPAP pressure that should restore stability to the airway, and similarly a correspondingly small decrease in the CPAP pressure when stability has so been restored. By being able to maintain the increases to such a small level, the patient is less likely to be woken, and will also benefit from avoiding apneas with their associated health risks.

For example, when shape factor 1 is below 1.0, the CPAP pressure is increased in proportion to the amount of the ratio being below 1.0. An increase of 1 cm $H_2O$ per breath per unit below a ratio of 1.0 has been found particularly effective. Conversely, if the ratio is above 1.0, the CPAP pressure is gradually reduced with a time constant of 20 minutes. If shape factor 2 is below 0.2, the CPAP pressure is increased at a rate of 1 cm $H_2O$ per breath per unit below 0.2. Conversely, if the shape factor is above 0.2 units, the pressure is gradually lowered with a time constant of 20 minutes.

An example of experimental validation involved a subject with severe Obstructive Sleep Apnea syndrome placed on nasal CPAP therapy. A catheter tip pressure transducer was placed in the hypopharyngeal space, below the site of upper airway obstruction, and the peak upper airway pressure gradient (UAP) from hypopharynx to mask calculated for each breath.

Figure 8A:
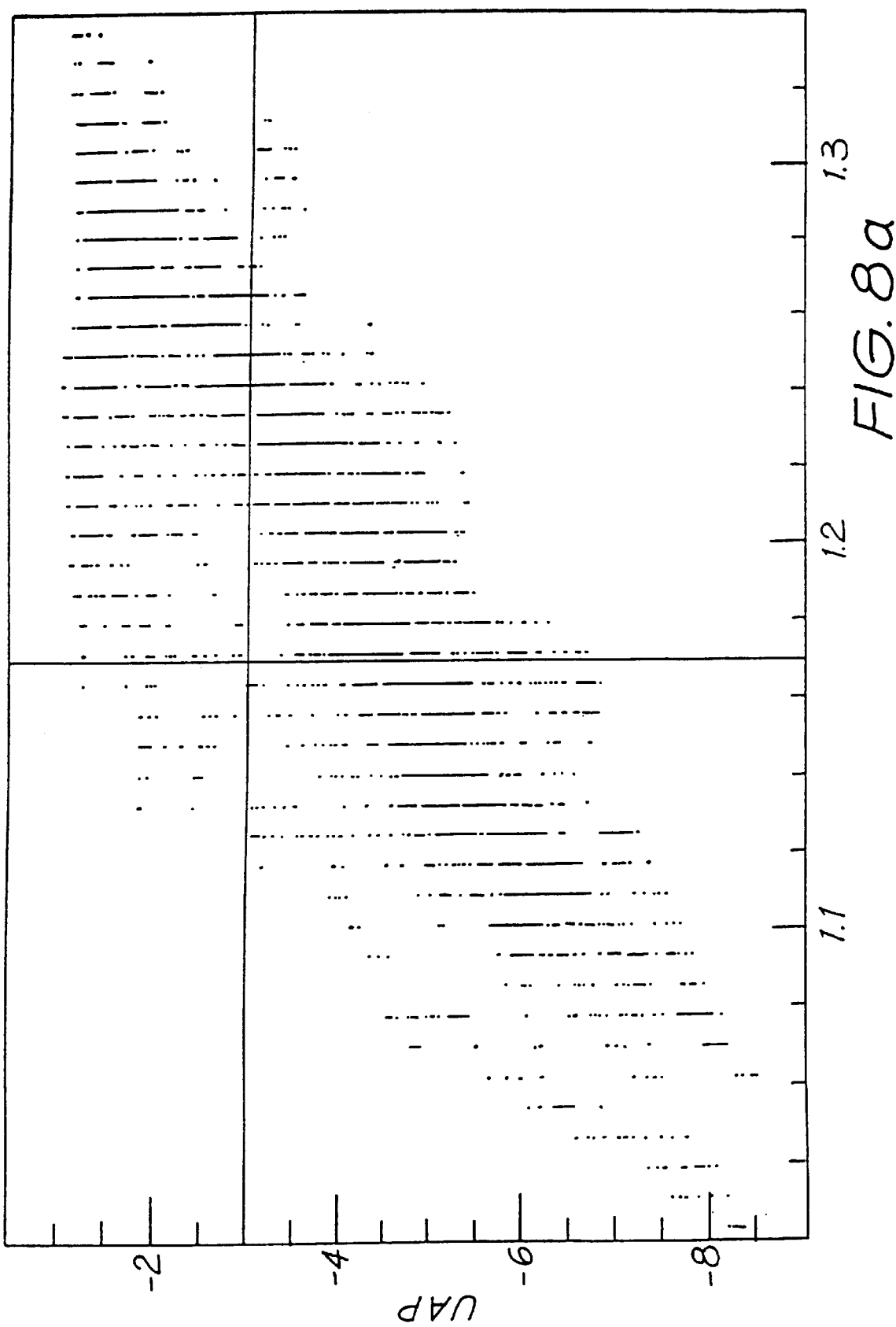
FIGS. 8a and 8b show clinical data of CPAP treatment utilising the shape factor methodologies.
Figure 8B:
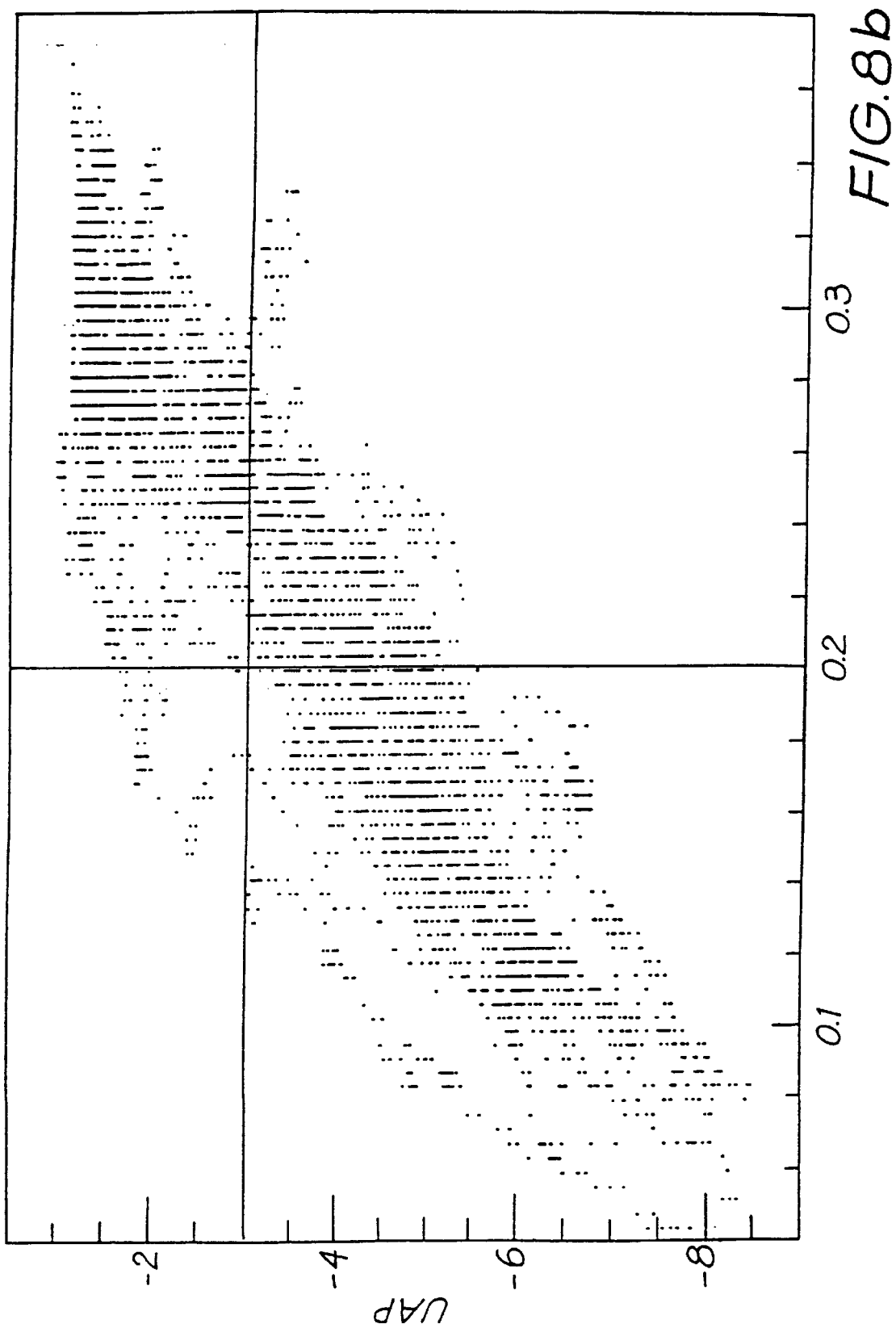

The CPAP pressure was intentionally reduced from time to time during stable sleep, in order to produce partial upper airway obstruction. For each breath taken during the night, the two shape factors were calculated, and plotted against the UAP, measured in cm $H_2O$. The results are shown in FIGS. 8*a* and 8*b*.

In this patient there was an 83% correlation between shape factor 1 (FIG. 8*a*) and UAP, with low values of shape parameter one associated with a high pressure drop across the upper airway, indicating partial obstruction. Similarly, there was an 89% correlation between shape factor 2 (FIG. 8*b*) and UAP.

The function achieved by shape factor 1 also can be achieved by an improved methodology in the detection of snoring.

Prior art U.S. Pat. No. 5,245,995 describes signal processing of the mask flow signal to determine a snore characteristic, particularly as shown in FIGS. 9 and 10 of that document. The respiratory air flow signal is bandpass filtered in the range 30–300 Hz. Snoring exhibits characteristic frequencies in this range, and as described in the prior art reference the sound intensity of snoring is indicative of almost complete obstruction of the airway. Thus CPAP pressure is increased if the snore signal is in excess of a snore threshold value. This then corresponds to the degree of obstruction otherwise detected by shape factor 1.

Although the snore detector and CPAP treatment effected in consequence of the occurrence of snoring operates satisfactorily, there is still scope for improvement. Once particular problem comes in that some CPAP apparatus caused wind noise occurs in the 30–300 Hz range, as does background noise due to the motor driving the blower.

As described herein, the digitized flow signal $f_n$ has been arrived at in a similar manner to that described in prior art U.S. Pat. No. 5,245,995, and thus includes snore component frequencies.

The methodology to improve performance of the snore detector firstly involves a determination of the blower motor speed. This can be achieved by a tachometer located on the motor. Then follows a determination of an expected flow signal such as would occur in the absence of snoring. This is calculated as a function of motor speed and airflow by the following formula:

$$\text{predicted signal} = k_1\omega + k_2\omega^2 + k_3 f + k_4 \frac{df}{dt}.$$

where $\omega$ is the motor speed signal and f is the flow signal. The constants $k_1$–$k_4$ are determined empirically. The predicated signal is then subtracted from the measured flow signal to obtain the snore signal. Thus the corrected snore signal more accurately reflects the occurrence and extent of snoring, and when compared against the snore threshold results in an increase in the CPAP pressure.

C. Determination of Airway Patency

If the outcome of step 14 is "Yes", then an apnea in progress. In accordance with the methodology of FIG. 1, a determination of airway patency (step 20) is made. Two methods are now described. The first is a measurement by cardiogenic airflow, and the second is an externally induced oscillation technique.

1. Cardiogenic Airflow

With each beat of the heart, of the order of 66 ml of blood is ejected from the chest over about 0.3 sec, producing a pulsatile blood flow out of the chest of the order of 0.22 l/sec peak flow. If the chest wall were rigid this would create a partial vacuum in the chest cavity, and, if the upper airway were open and of zero resistance, a similar quantity of air would be sucked in through the trachea.

In practice, the chest wall is not totally rigid, and the upper airway has a finite resistance. Consequently the observed airflow with each beat of the heart is of the order of 0.02 to 0.1 l/sec. If there is a central apnea with an open airway, there will be a very small pulsatile airflow of the order of 0.02 to 0.1 l/sec in time with the heart beat. Conversely, if the airway is closed, there will be no pulsatile airflow in time with the heart beat.

Figure 9A:
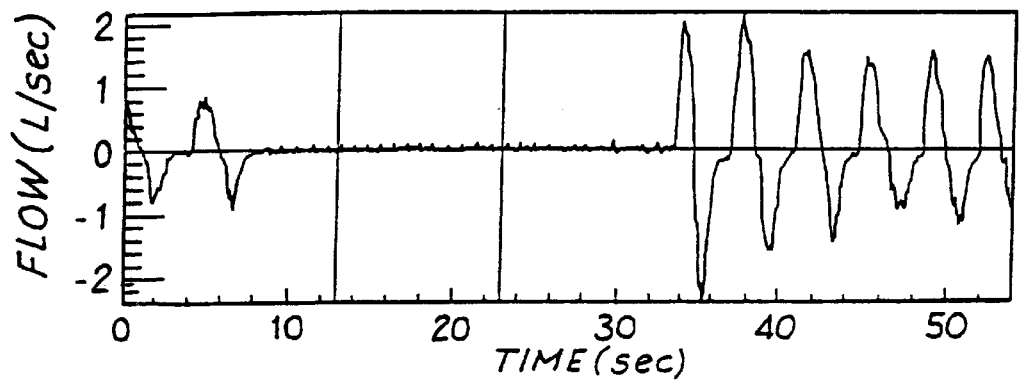
FIGS. 9a–9c and 10a–10c show clinical respiratory air flow and frequency signals during an apnea.
Figure 9B:
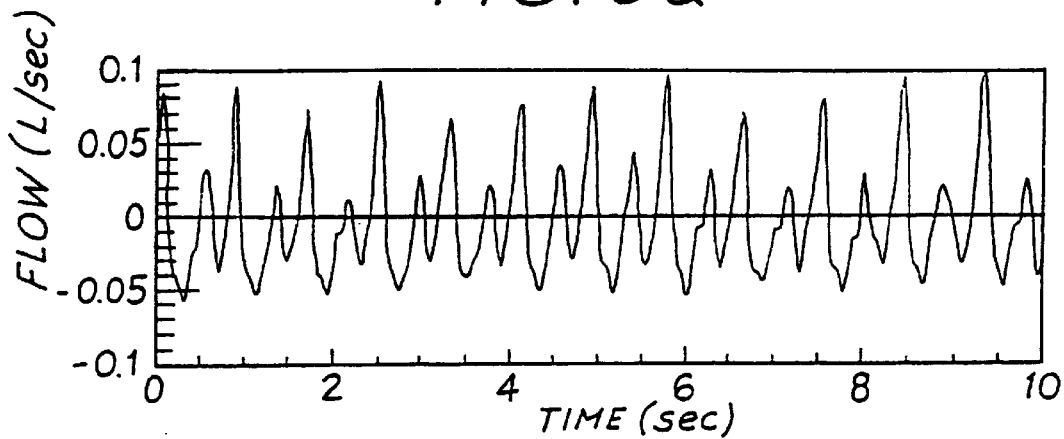
Figure 9C:
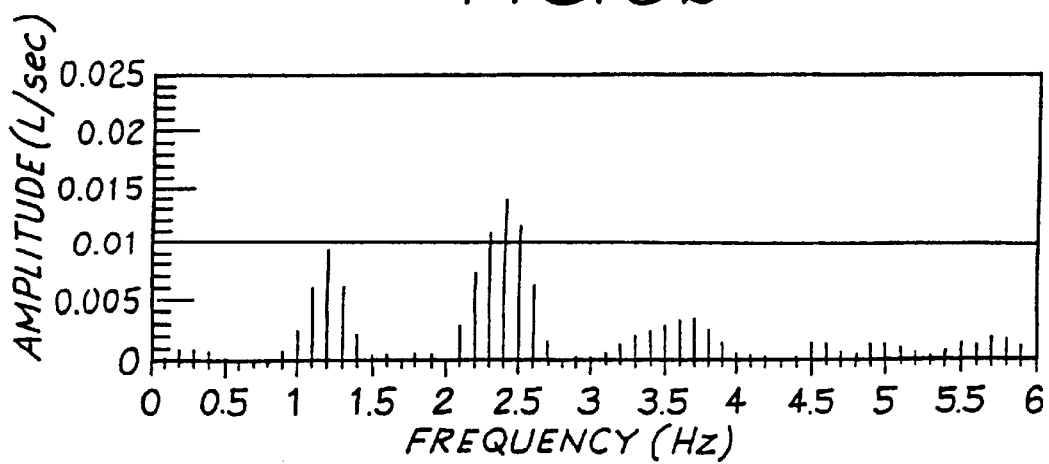
Figure 10A:
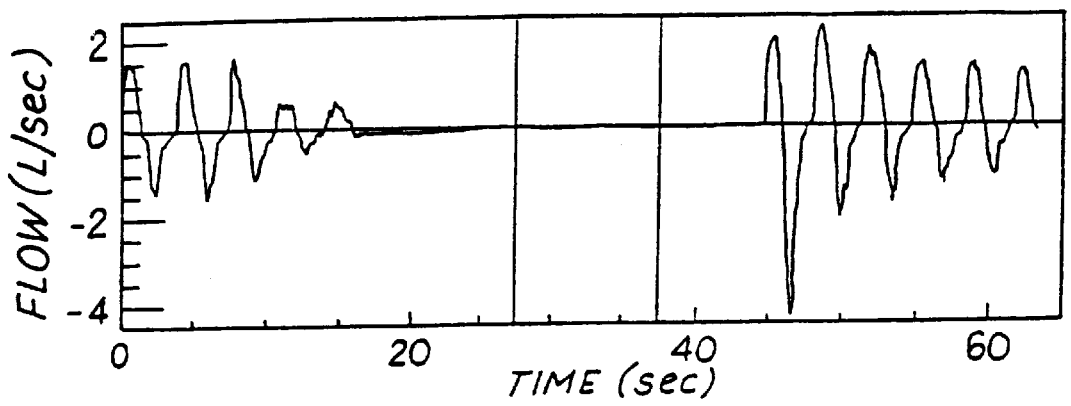
Figure 10B:
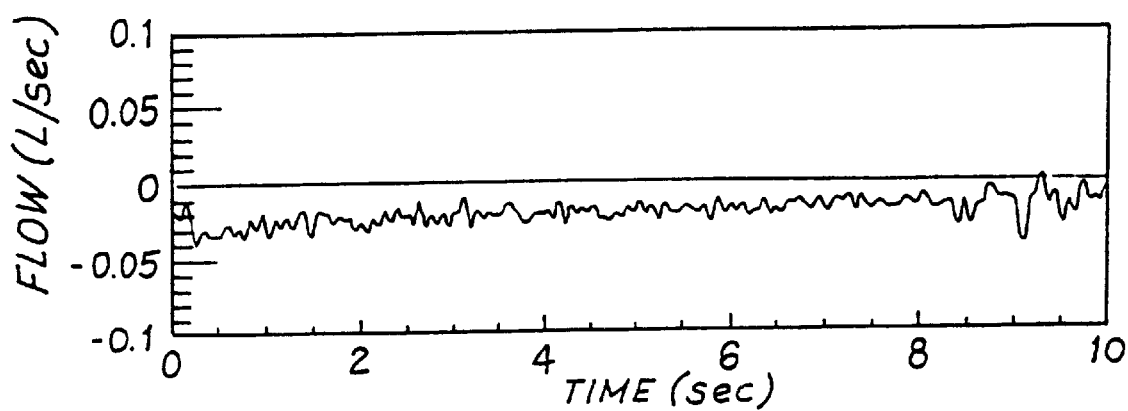
Figure 10C:
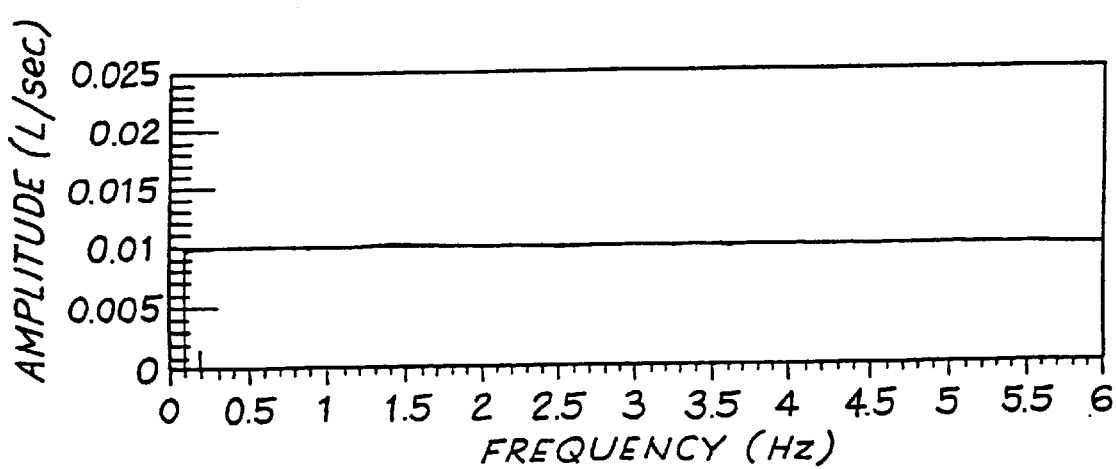

FIGS. 9a–9c represent a central apnea with an open airway lasting approximately 30 seconds, determined from diaphragm electromyogram tracings (not shown). Conversely, FIGS. 10a–10c represent an obstructive apnea with a closed airway. FIGS. 9a and 10a respectively show a respiratory airflow signal, f(t), during which an apnea lasting approximately 25 seconds occurs, indicated by a near cessation of airflow.

FIGS. 9b and 10b respectively show a ten second close-up (between t=11.5 s to t=21.5 s) of the airflow signal during the apnea. It can be noted that in FIG. 9b, where the airway is open, small rhythmic oscillations in the airflow are seen, with the expected peak flow of about 0.1 l/sec. Inspection of the corresponding electrocardiogram (not shown) confirms that these oscillations are of cardiac origin, with airflow either phase-locked with the heartbeat, or at exactly double the cardiac rate. Conversely, in FIG. 10b, there is either no airflow at all, or at least irregular airflow due to not quite complete obstruction.

FIGS. 9c and 10c respectively show the discrete Fourier transform of FIGS. 9b and 10b. In FIG. 9c (open airway), there are strong peaks in the frequency spectrum at around 1.25 Hz and/or 2.5 Hz corresponding to the heart rate and its first harmonic. The peaks reach an amplitude of at least 0.01 l/sec. Conversely, in FIG. 10c (closed airway), the discrete Fourier transform shows little or no activity between 0.75 and 3 Hz.

Figure 11:
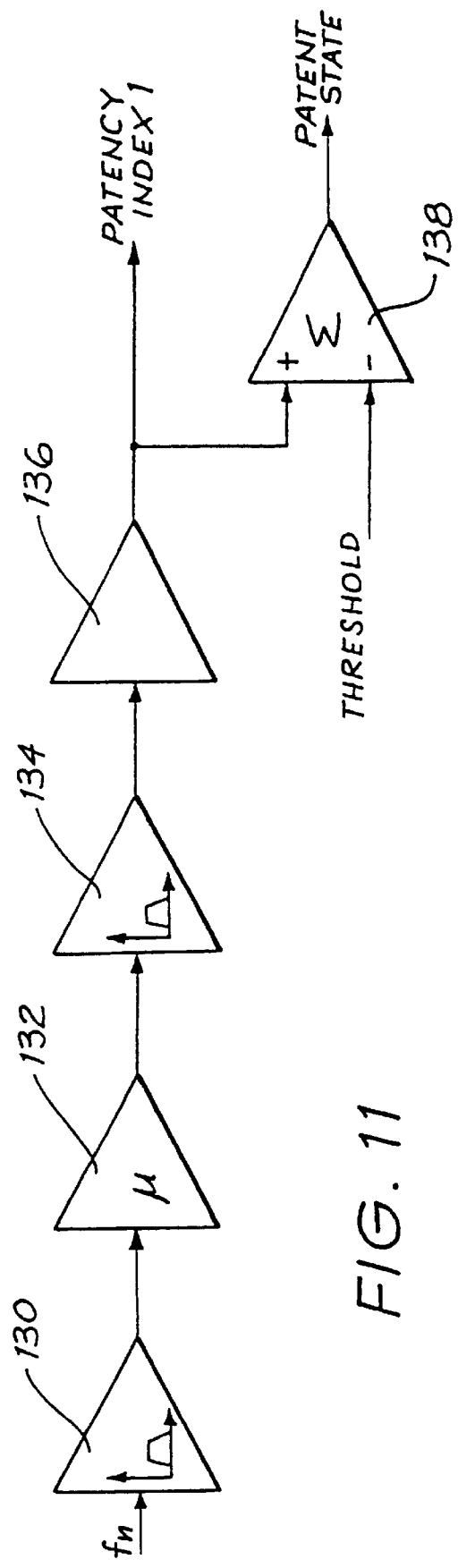
FIG. 11 shows a flow diagram for the cardiogenic determination of patency.

The methodology firstly records the airflow, f(t), using by the flow transducer 48 shown in FIG. 2 or FIG. 3. The signal is digitized, for example at 50 Hz, using the analog-to-digital converter (ADC) 54, and sampled by the controller 62. The subsequent processing steps are shown in FIG. 11.

If required, the flow signal, $f_n$, is digitally bandpass filtered by the bandpass filter 130 between 0.1 and 6 Hz to remove low frequency components (leak) and high frequency components (noise) to yield a clean respiratory air flow signal.

The occurrence of an apnea will have previously been determined by, for example, the Breathing Index derived in FIG. 5. In that case the process continues.

A Discrete Fourier transform (DFT) is performed, by the processing element 132, of the airflow signal fn during the apnea. Only terms up to 6 Hz need to be calculated. In the case where the heart rate is not known, processing is as follows: if the amplitude of the DFT exceeds a Threshold value of 0.01 l/sec, as determined by the peak height detector 136 and the subsequent comparator element 138, at any frequency between 0.75 and 3 Hz (bandpass element 134), the airway is declared open; otherwise it is declared closed. Patency Index 1 represents the output of the peak height detector 136.

If an electrocardiogram or other indicator of heartbeat, such as a pulse oximeter is available, then an appropriate method is to:

(1) Use a digital or electronic trigger to trigger on each heart beat.

(2) Accumulate the respiratory airflow signal at time nT after receipt of each trigger into element n of an array, summing with previous values at time nT for the duration of the apnea.

(3) Divide by the number of heartbeats to obtain the average air flow as a function of time into the heartbeat.

(4) Calculate the first two terms of the DFT of this signal (fundamental and first harmonic) and inspect for an amplitude of the order of 0.1 l/sec.

In such a case where the heart rate is known, then only the amplitudes at the heart rate and its first harmonic need be considered, leading to a more accurate estimation.

Instead of using the DFT, any suitable mathematical method of detecting a rhythmic oscillation with a frequency of the anticipated heart rate and its first harmonic (0.75 to 3 Hz) will suffice. Such methods could include measuring the regularity of peak heights and zero crossings, autocorrelation, or other digital filtering methods.

2. Externally Induced Oscillations

If the airway is open, but the respiratory muscles are relaxed (i.e. a central apnea with open airway), then small externally originating fluctuations in the mask pressure will induce a small respiratory airflow by inflating and deflating the lungs, and by compressing and decompressing the gas in the lungs. Conversely, if the airway is closed, no airflow will be induced.

FIG. 12a shows a respiratory airflow signal as a function of time during nasal CPAP therapy. In the first half of the tracing, there is a central apnea with open airway lasting approximately 22 seconds. FIG. 12b shows that the CPAP pressure is approximately 15.5 cm $H_2O$. The high frequency "noise" apparent through most of the pressure trace is largely due to cardiogenic airflow as previously discussed.

Approximately 5 seconds into the apnea a 2 Hz, 1 cm $H_2O$ pressure oscillation is induced (applied) for 6 seconds (i.e. between t=14 s to t=20.5 s). It can be seen that this pressure modulation induces a corresponding 2 Hz modulation in the respiratory air flow signal. FIGS. 12c–12d are an enlargement of the period of testing. The respiratory air flow signal has an amplitude of approximately +0.2 l/sec.

Conversely, in FIGS. 13a–13d there is an obstructive apnea, with a closed airway. A similar tracing would be seen with a central apnea with a closed airway. It can be seen that in this case there is no obvious induced flow signal during the 6 second period of 2 Hz pressure oscillations. The mean induced signal was 0.01 l/sec.

Figure 14:
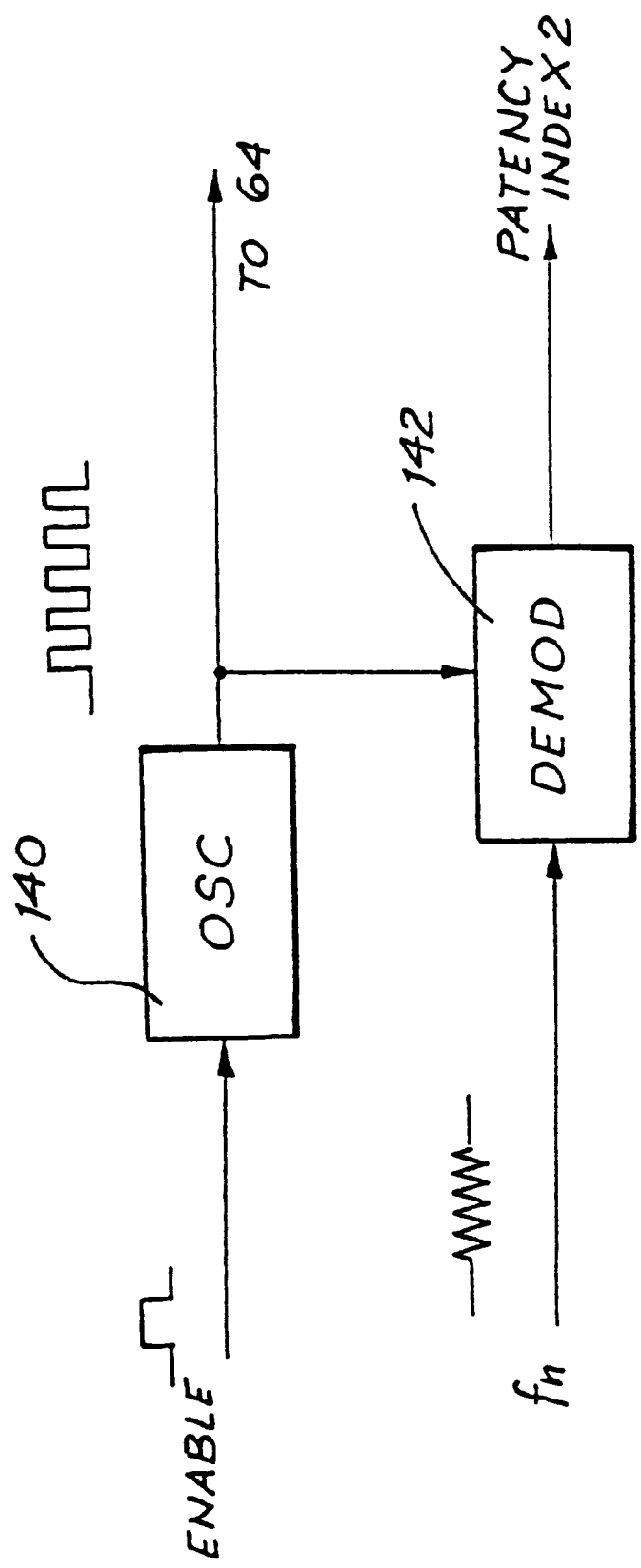
FIG. 14 shows a flow diagram of an applied modulated output in the determination of patency.

The procedure is typically, at 4–6 seconds into the apnea, the CPAP pressure generator output pressure supplied to the motor-servo unit 40 is controlled to produce a modulated pressure output. As shown in FIG. 14, the output from the generation element 140 (controller 62) is a signal modulated with a low amplitude square wave, typically at 2–4 Hz. This produces a quasi-sinusoidal oscillation in the mask pressure, with a typical amplitude of 0.5–1 cm $H_2O$.

As further shown in FIG. 14, the air flow induced by the pressure modulation is separated from air flow induced by other factors (such as heartbeat), by demodulating the measured air flow signal, $f_n$, by a demodulator 142 with the 2 Hz driving signal. The components at 0 degrees and 90 degrees to the output signal are calculated, and their amplitudes are added vectorially to yield a mean induced air flow signal amplitude (Patency Index 2). The mean signal in this case is 0.12 l/sec.

Apneas are classified as "airway open" if the mean induced signal is more then 0.03 l/sec, and "airway closed" if the mean induced signal is less than 0.03 l/sec. Alternatively, the mean induced signal could be divided by the amplitude of the inducing pressure to yield the conductance (degree of openness) as a continuous variable.

Figure 15:
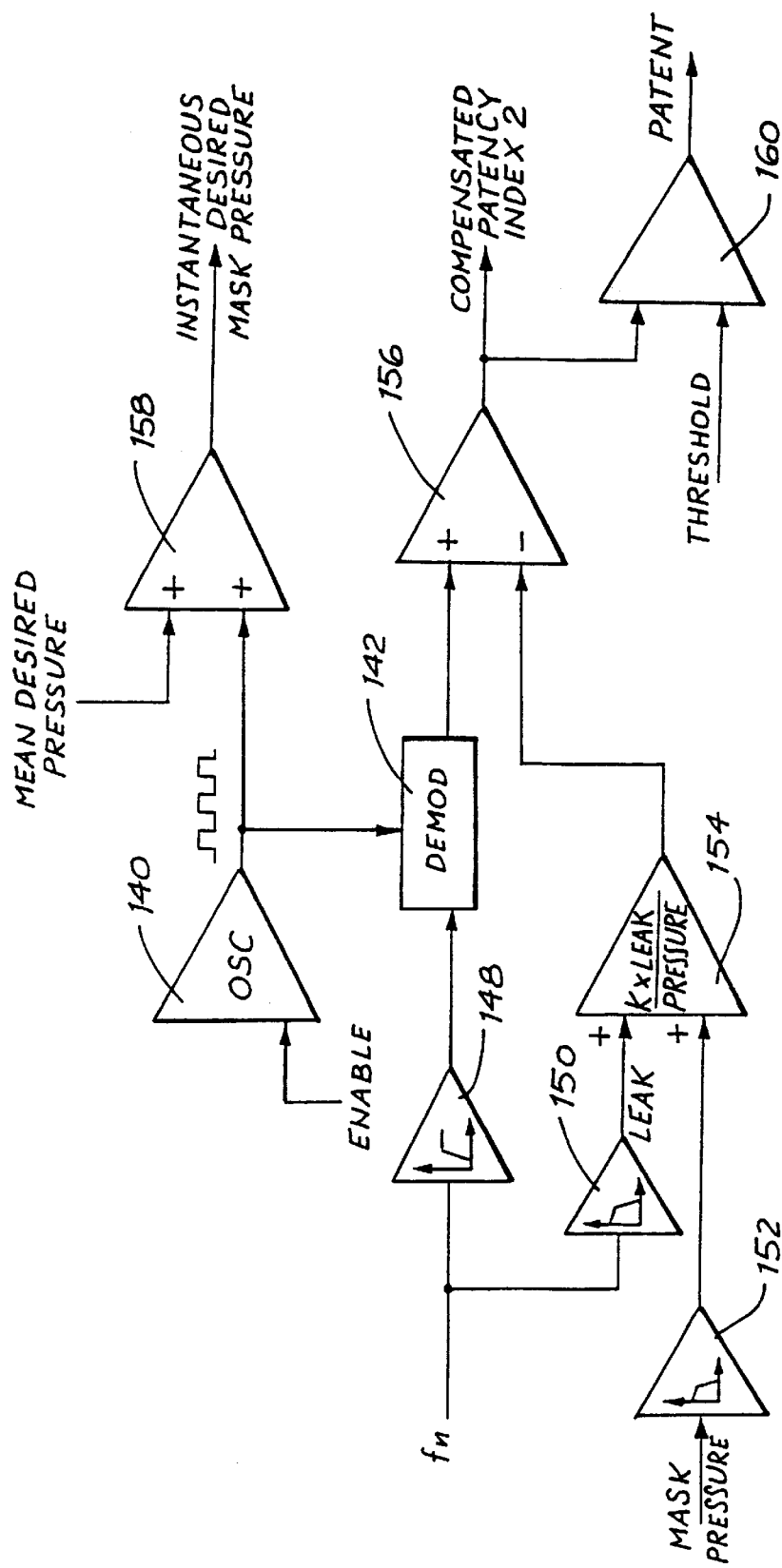
FIG. 15 shows a flow diagram of leak compensated patency determination.

When it is desired to determine the state of the airway in the presence of typical CPAP treatment, it is preferable to take into account the effect of mask leaks. A leak between the mask and the face can produce a false positive induced air flow signal. As shown in FIG. 15, the oscillator 140 induces the low-frequency, low amplitude pressure oscillations as previously described. The air flow signal $f_n$ is high pass filtered by the high pass filter 148 (typically 0.1 Hz) to remove leak, and passed to the demodulator 146, which produces Patency Index 2 as previously described.

The flow signal is also low pass filtered (typically 0.1 Hz) by the low pass filter 150 to derive a measurement of leak. The value calculated in step 142 represents the sum of the induced signal due to modulation of respiratory air flow and the induced signal due to modulation of flow through the leak. The induced signal due to modulation of flow through the leak is then calculated by arithmetic element 154, as:

$$\frac{0.5 \cdot \text{leak} \cdot \text{inducing oscillation amplitude}}{\text{mean mask pressure}}.$$

This is then subtracted by the subtractor 156 from the uncompensated Patency Index to produce a leak-compensated Patency Index. The leak-compensated Patency Index can optionally be divided by the inducing oscillation amplitude to yield airway conductance, as described previously.

In the case of either methodology utilised to determine patency, if the result of that determination (step 20) is "No", then as was the case for a partial obstruction, the CPAP treatment pressure is increased. If the result is "Yes", then a central apnea with an open airway is occurring, and it is inappropriate to increase CPAP pressure. Instead the event is only logged, and step 17 follows, whereby CPAP pressure is reduced, as has previously been discussed.

3. Extensions to the Methodology of Determining Patency.

(1) Instead of declaring the airway open or closed, the airway can be declared open to a certain degree. For example, if the peak amplitude of the DFT was 50% of the threshold, the airway is taken as being patent to degree 0.5. Similarly with the externally induced oscillation method.

(2) Instead of using the entire duration of the apnea, calculations can be performed on a moving window of appropriate duration, such as 10 seconds. In this way, mixed apneas, in which the airway is open for only part of the apnea, can be detected.

(3) Other methods of measuring or inferring respiratory airflow can be utilised. For example, instead of measuring mask airflow with a flow-resistive element and differential pressure transducer, mask airflow could be measured using an ultrasonic flow transducer, or inferred from mask pressure, using a single ended pressure transducer. Alternatively, measurements of chest wall and/or abdominal movement (such as magnetometers, inductance plethysmography, or strain gauges) could be used.

D. A Combined System for Automatic Adjustment of CPAP Pressure

Figure 16:
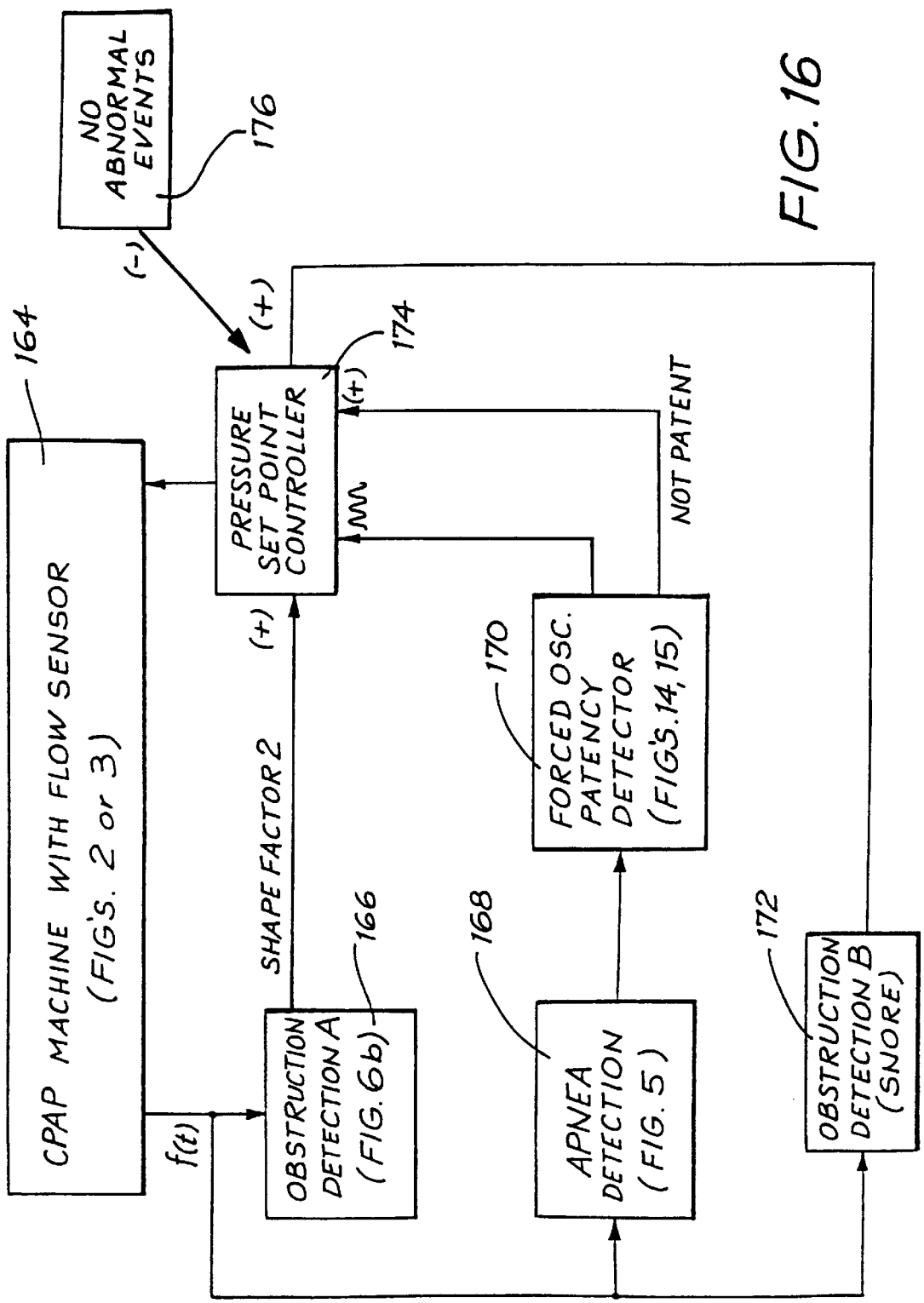
FIG. 16 shows, in schematic form, a preferred CPAP treatment system.
Figure 6A:
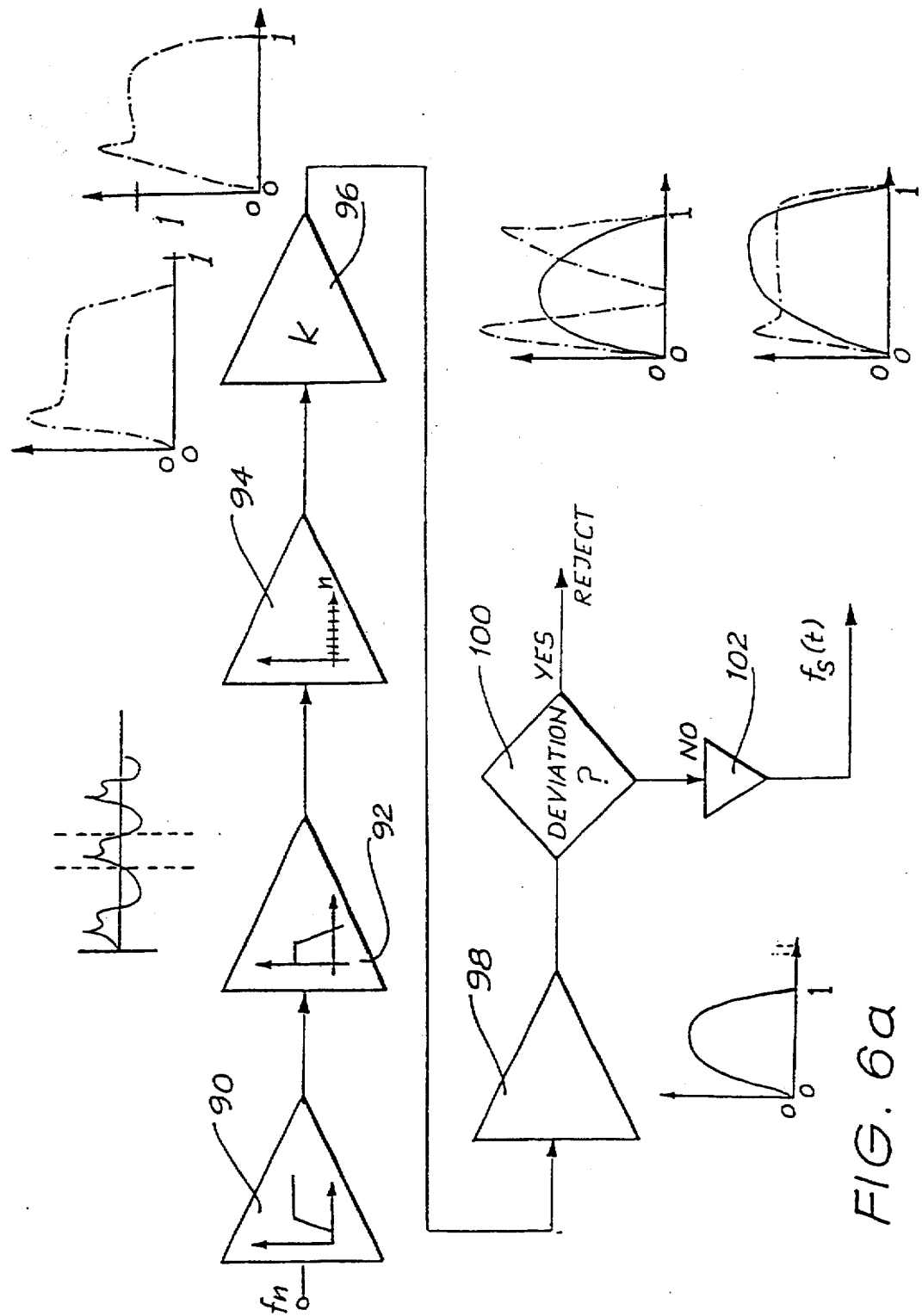

FIG. 16 illustrates, in schematic block form, a particular preferred embodiment of CPAP treatment apparatus. The CPAP machine 164 represents the component element shown in FIG. 2 or FIG. 3 except for the elements bearing the reference numerals 54,58,60 and 62. All of the logic blocks 166–176 are processing steps implemented in a microcontroller, which, in FIG. 2, is referred to by the reference numeral 62. The embodiment implements a hierarchic methodology, based around the methodology of FIG. 1, that allows the progressive use of pre-obstructive and obstructive indications to trigger CPAP treatment pressure increases of magnitude and duration appropriate for the severity of the event.

The mask pressure is initially set to a low pressure, typically 4 cm $H_2O$. Whenever the apnea detector 168 detects an apnea, the airway patency detector 170 determines whether the airway is open or closed by the forced oscillation method, and if closed, the mask pressure is increased, typically by 1 cm $H_2O$ per 15 seconds of apnea. If a central apnea is occurring, no increase in CPAP pressure is instructed.

If a snore is detected by the snore detector 172 (such as that disclosed in U.S. Pat. No. 5,245,995) the mask pressure is also increased. If the snore index on the given breath exceeds a critical threshold value, the pressure is increased by 1 cm $H_2O$ per unit above the threshold value. The defaults threshold for the snore index is 0.2 units, corresponding approximately to a snore that can only just be reliably detected by a technician standing at the bedside. The rate of rise in pressure is limited to a maximum of 0.2 cm $H_2O$ per second, or 12 cm $H_2O$ per minute.

In some patients, it is not possible to prevent the occasional snore, even at maximum pressure. Consequently, above pressures of 10 cm $H_2O$, a heuristic methodology is used to perform a trade-off between the possible advantage of increasing the pressure and the disadvantage of increased side effects. Thus the threshold is adjusted as follows:

| Pressure (cm H₂O) | Threshold (snore units) | Description |
|---|---|---|
| <10 | 0.2 | very soft |
| 10–12 | 0.25 | |
| 12–14 | 0.3 | soft |
| 14–16 | 0.4 | |
| 16–18 | 0.6 | moderate |
| >18 | 1.8 | loud |

If the shape factor 2 is less than the threshold value, the mask pressure also is increased. The default threshold value is 0.15 units. The default rate of increase of pressure is such that a severely abnormal shape factor of 0.05 units will produce a rise in pressure of 0.3 cm H₂O per breath, or approximately 4.5 cm H₂O per minute.

The lips and tongue can sometimes act like a one-way valve, forming a seal during inspiration when the pharyngeal pressure is lowest but failing during early to mid-expiration when the pressure is highest. Large leaks, and particularly valve-like leaks, can cause the shape factor to read low, falsely implying flow limitation. To compensate for this, the default threshold is increased according to an empiracal heuristic technique if there is a large leak, or if there is a valve-like leak. This is to avoid the treatment pressure being increased unnecessarily. Consequently, in the presence of a large leak, more reliance is placed on the snore and apnea detectors.

In some patients, the shape factor does not become normal even at maximum pressure. Consequently, a further heuristic trade-off is made between possible increases in patency within increasing pressure, versus increasing side effects.

The heuristics used are as follows:

(i) If the leak exceeds 0.7 l/sec, the critical threshold for the shape factor is 0. In the range 0.3–0.7 l/sec, the threshold is decreased proportionately, so that as the leak increases more severe flattening is required before the pressure will rise.

(ii) An index of the presence of valve-like leaks is calculated as the ratio of the peak flow during the first 0.5 seconds of expiration to the mean flow during the second 0.5 seconds of expiration. If this ratio exceeds 5:1, the threshold is 0. In the range 4:1 to 5:1, the threshold is reduced proportionately.

(iii) If the mask pressure is 20 cm H₂O, the threshold is 0, and is reduced proportionately in the range 10–20 cm H₂O. For example, if the leak is 0.4 l/sec, and the mask pressure is 15 cm H₂O, the threshold is reduced by 25% because of the leak, and a further 50% because of the already high treatment pressure so that the new threshold is 0.056 units. Conversely, if no abnormality is detected on a particular breath (block 176), the mask pressure is reduced with an appropriate time constant, typically 10–20 minutes per cm H₂O for snore or shape factor changes, and preferably, about 40 minutes per cm H₂O following apneas.

The preferred embodiment of the combined system for automatic adjustment of CPAP treatment pressure described above was used to treat 28 patients with previously untreated obstructive sleep apnea syndrome. CPAP pressure commenced at 4 cm H₂O, and increased automatically in response to closed airway apneas, snoring, and inspiratory air flow limitation. The following table compares results with those obtained in the same subjects without treatment:

| | Untreated (mean ± SEM) | Treated (mean ± SEM) |
|---|---|---|
| Apnea Index (events/hr) | 35.5 ± 5.9 | 1.5 ± 0.32 |
| Time in Apnea (Percent of night) | 24.5 ± 4.7 | 1.0 ± 0.37 |
| Slow Wave Sleep (Percent of night) | 7.0 ± 1.6 | 20.0 ± 2.2 |
| REM Sleep (Percent of night) | 9.4 ± 1.4 | 20.3 ± 2.1 |
| Arousal Index (Events/hr) | 55.9 ± 5.3 | 10.8 ± 1.9 |
| Respiratory Arousals (Events/hr) | 51.5 ± 5.4 | 4.2 ± 1.5 |

There was a dramatic reduction in the number of apneas per hour, and the percentage of time in apnea. There was a large increase in the percentage of deep restorative sleep (slow wave and REM sleep). There was a dramatic reduction in the number of arousals from sleep, particularly those of a respiratory origin. These results confirm that the combined system produces excellent results in treating obstructive sleep apnea syndrome.

The system described can also be utilised in a diagnostic mode, typically where nasal cannulae are utilized in the place of a mask arrangement sealed to the patient's face. In this mode, measurements of apneas, patency, and partial obstruction are logged, but no CPAP treatment is effected. The nasal cannulae are connected to one side of the flow sensor 50 in FIG. 2. Only elements 50, 54, 56, 58, 60 and 62 are required in this mode. Since with nasal cannulae, the signal from the flow transducer 50 is not linear with flow, there is an additional step in which the signal from the flow transducer is linearized, preferably by use of a lookup table in the microcontroller 62. The data collected provides the physician with the ability to diagnose conditions such as Obstructive Sleep Apnea syndrome and Upper Airway Resistance syndrome.

Numerous alterations and modification, as would be apparent to one skilled in the art, can be made without departing from the basic inventive concept.

More complex variants of CPAP therapy, such as bi-level CPAP therapy or therapy in which the mask pressure is modulated within a breath, can also be monitored and/or controlled using the methods described herein.

The moving average variance apnea detector, as described, can be extended to include a hypopnea detector by adding a second comparator set at a higher threshold, so that it will respond to partial reductions in ventilation.

What is claimed:

1. A method for determining the degree of obstruction of the airway of a patient receiving continuous positive airway pressure (CPAP) treatment by apparatus for supplying CPAP to the patient's airway, the method comprising the steps of:

measuring respiratory air flow from the patient to give an air flow signal;

filtering said air flow signal to reject components at least due to respiration to give a filtered air flow signal having components due to patient snoring and noise of said CPAP apparatus;

predicting a CPAP apparatus noise component of said filtered air flow signal; and subtracting said predicted noise component from said filtered air flow signal to give a snore component signal as a measure of the degree of obstruction of the airway.

2. A method as claimed in claim 1, wherein the filtering step includes bandpass filtering also to reject high frequency noise components.

3. A method for determining patency of the airway of a patient, the method comprising the steps of:

applying an oscillatory pressure waveform of known frequency to the patient's airway;

measuring respiratory air flow from the patient; and determining that the airway is patent if there is a component of said air flow at said known frequency induced by said oscillatory pressure waveform.

4. A method as claimed in claim 3, wherein said air flow component is determined from the amplitude of said air flow signal, and comprising the further step of comparing said magnitude with a threshold value, and if said magnitude is greater than said threshold value then the airway is declared patent.

5. A method for determining the occurrence of an apnea in a patient, the method comprising the steps of:

measuring respiratory airflow from the patient as a function of time;

determining the variance of said measured airflow; and determining from said variance that an apnea is occurring.

6. A method as claimed in claim 5, wherein said variance is a moving average variance over said time window.

7. A method for determining the occurrence of an apnea in a patient, the method comprising the steps of:

measuring respiratory airflow from the patient as a function of time;

determining a variance of said measured airflow, wherein said variance is a moving average variance over time;

determining from said variance that an apnea is occurring; and comparing said moving average variance with a threshold value, and if said moving average variance falls below said threshold value, then an apnea is occurring.

8. A method as claimed in claim 7, wherein said measured airflow is expressed as an airflow signal.

9. A method as claimed in claim 8, whereby said step of measuring includes sampling said respiratory airflow at equally spaced points in time to give a sampled airflow signal.

10. A method as claimed in claim 7, whereby, in said comparing step, said variance must fall below said threshold value for a predetermined period of time before it is determined that an apnea is occurring.

11. A method as claimed in claim 7, comprising the further step of either commencing continuous airway pressure (CPAP) treatment or increasing CPAP treatment pressure to the patient if an apnea is occurring.

12. Apparatus for determining the occurrence of an apnea in a patient, the apparatus comprising;

means for measuring respiratory airflow from the patient as a function of time;

means for determining the variance of said measured airflow; and means for determining from said variance that an apnea is occurring.

13. Apparatus for determining the occurrence of an apnea in a patient, the apparatus comprising:

a flow sensor in fluid communication with the entrance to patient's airways to output a signal representative of respiratory airflow as a function of time;

data processing means receiving said airflow signal, calculating the variance of said airflow signal, and comparing said variance against a threshold value to determine that an apnea is occurring if the threshold value is not exceeded.

14. Apparatus as claimed in claim 13, wherein the data processing mean calculates a moving average variance over a time window.

15. Apparatus for determining the occurrence of an apnea in a patient, the apparatus comprising:

a flow sensor in fluid communication with the entrance to patient's airways to output a signal representative of respiratory airflow as a function of time;

data processing means receiving said airflow signal, calculating a variance of said airflow signal, and comparing said variance against a threshold value to determine that an apnea is occurring if the threshold value is not exceeded, wherein the data processing means calculates said variance as a moving average variance over a time window; and sampling means receiving said airflow signal and sampling said signal into equally spaced discrete values to be passed to said data processing means.

16. Apparatus for the provision of CPAP treatment to the airways of a patient, the apparatus comprising:

a mask for the provision of breathable gas to the patient's airways;

a conduit in fluid communication with said mask;

a controllable flow generator to supply said breathable gas to said conduit at a controlled pressure elevated above atmospheric pressure;

a flow sensor in fluid communication with the entrance to the patient's airways to output a signal representative of respiratory airflow as a function of time; and data processing means receiving said airflow signal and controlling said flow generator and hence said controlled pressure, the data processing means calculating the variance of said airflow signal, comparing said variance against a threshold value to determine that an apnea is occurring if the threshold value is not exceeded, and, in that case, causing said flow generator to increase the controlled pressure.

17. Apparatus as claimed in claim 16, wherein the data processing means calculates a moving average variance over a time window.

18. Apparatus for the provision of CPAP treatment to the airways of a patient, the apparatus comprising:

a mask for the provision of breathable gas to the patient's airways;

a conduit in fluid communication with said mask;

a controllable flow generator to supply said breathable gas to said conduit at a controlled pressure elevated above atmospheric pressure;

a flow sensor in fluid communication with the entrance to the patient's airways to output a signal representative of respiratory airflow as a function of time;

data processing means receiving said airflow signal and controlling said flow generator and hence said controlled pressure, the data processing means calculating a variance of said airflow signal, comparing said variance against a threshold value to determine that an apnea is occurring if the threshold value is not exceeded, and, in that case, causing said flow generator to increase the controlled pressure, wherein the data processing means calculates the variance as a moving average variance over a time window; and sampling means receiving said airflow signal and sampling said signal into equally spaced discrete values to be passed to said data processing means.

19. Apparatus for the provision of bi-level CPAP treatment to the airways of a patient, the apparatus comprising:

a mask for the provision of breathable gas to the patient's airways;

a conduit in fluid communication with said mask;

a controllable flow generator to supply said breathable gas to said conduit at a controlled inspiratory pressure and a controlled expiratory pressure in synchronism with patient respiratory phases;

a flow sensor in fluid communication with the entrance to the patient's airways to output a signal representative of respiratory airflow as a function of time; and data processing means receiving said airflow signal, detecting therefrom the change of state in patient respiration to control said flow generator and hence said controlled inspiratory and expiratory pressures, the data processing means further calculating the variance of said airflow signal, comparing said variance against a threshold value to determine that an apnea is occurring if the threshold value is not exceeded, and, in that case, causing said flow generator to increase either one or both of said inspiratory and expiratory pressures.

20. Apparatus as claimed in claim 19, wherein the data processing mean calculates a moving average variance over a time window.

21. Apparatus for the provision of bi-level CPAP treatment to the airways of a patient the apparatus comprising:

a mask for the provision of breathable gas to the patient's airways;

a conduit in fluid communication with said mask;

a controllable flow generator to supply said breathable gas to said conduit at a controlled inspiratory pressure and a controlled expiratory pressure in synchronism with patient respiratory phases;

a flow sensor in fluid communication with the entrance to the patient's airways to output a signal representative of respiratory airflow as a function of time;

data processing means receiving said airflow signal, detecting therefrom the change of state in patient respiration to control said flow generator and hence said controlled inspiratory and expiratory pressures, the data processing means further calculating a variance of said airflow signal, comparing said variance against a threshold value to determine that an apnea is occurring if the threshold value is not exceeded, and, in that case, causing said flow generator to increase either one or both of said inspiratory and expiratory pressures, wherein the data processing means calculates said variance as a moving average variance over a time window; and sampling means receiving said airflow signal and sampling said signal into equally spaced discrete values to be passed to said data processing means.

\* \* \* \* \*

UNITED STATES PATENT AND TRADEMARK OFFICE
CERTIFICATE OF CORRECTION

PATENT NO. : 6,138,675
DATED : October 31, 2000
INVENTOR(S) : Berthon-Jones

It is certified that error appears in the above-identified patent and that said Letters Patent is hereby corrected as shown below:

Claim 14,
Line 2, change "mean" to -- means --;

Claim 20,
Line 2, change "mean" to -- means --.

Drawings,
Substitute sheet 6 of 20, Fig. 6a consisting of the amendment to the drawing approved by the examiner (copy is enclosed) for the sheet 6 of 20, Fig. 6a printed with the patent.

Signed and Sealed this

Sixth Day of November, 2001

Attest:

NICHOLAS P. GODICI
*Attesting Officer*   *Acting Director of the United States Patent and Trademark Office*